(12) United States Patent
McCormack et al.

(10) Patent No.: US 10,201,375 B2
(45) Date of Patent: Feb. 12, 2019

(54) LATERAL MASS FIXATION SYSTEM

(71) Applicants: Bruce M. McCormack, San Francisco, CA (US); Edward Liou, Pleasanton, CA (US); Shigeru Tanaka, Half Moon Bay, CA (US); Christopher U. Phan, Dublin, CA (US)

(72) Inventors: Bruce M. McCormack, San Francisco, CA (US); Edward Liou, Pleasanton, CA (US); Shigeru Tanaka, Half Moon Bay, CA (US); Christopher U. Phan, Dublin, CA (US)

(73) Assignee: PROVIDENCE MEDICAL TECHNOLOGY, INC., Pleasanton, CA (US)

( * ) Notice: Subject to any disclaimer, the term of this patent is extended or adjusted under 35 U.S.C. 154(b) by 0 days.

(21) Appl. No.: 14/723,410

(22) Filed: May 27, 2015

(65) Prior Publication Data

US 2015/0342649 A1    Dec. 3, 2015

Related U.S. Application Data

(60) Provisional application No. 62/004,143, filed on May 28, 2014.

(51) Int. Cl.
*A61B 17/70* (2006.01)
*A61B 17/16* (2006.01)
*A61B 17/17* (2006.01)

(52) U.S. Cl.
CPC ...... *A61B 17/7082* (2013.01); *A61B 17/1671* (2013.01); *A61B 17/1757* (2013.01);
(Continued)

(58) Field of Classification Search
CPC ............ A61B 17/7064; A61B 17/7062; A61F 2/4611
See application file for complete search history.

(56) References Cited

U.S. PATENT DOCUMENTS 1,934,962 A    11/1933   Barry
2,708,376 A     5/1955   Booth
(Continued)

FOREIGN PATENT DOCUMENTS

DE    G9304368.6 U1    5/2003
FR        2722980 A1    2/1996
(Continued)

OTHER PUBLICATIONS

US 7,063,700, 06/2006, Michelson (withdrawn)
(Continued)

*Primary Examiner* — Julianna N Harvey
(74) *Attorney, Agent, or Firm* — Dorsey & Whitney LLP

(57) ABSTRACT

A device for accessing and guiding at least one fixation device to a spine may include a distal portion configured to fit in a facet of the spine and a proximal portion extending from the distal portion. The proximal portion may be detachable from the distal portion and may be hollow or solid. A system for accessing and guiding at least one fixation device to a spine may include a distal portion configured to fit in a facet of the spine, a proximal portion extending from the distal portion, and a slidable guide device for sliding over the facet guide device to guide at least one instrument to the spine.

17 Claims, 22 Drawing Sheets

(52) U.S. Cl.
CPC ...... *A61B 17/7011* (2013.01); *A61B 17/7032* (2013.01); *A61B 17/1604* (2013.01); *A61B 17/7064* (2013.01)

(56) References Cited

U.S. PATENT DOCUMENTS

| | | | |
|---|---|---|---|
| 2,984,241 A | 5/1961 | Carlson |
| 4,479,491 A | 10/1984 | Martin |
| 4,530,355 A | 7/1985 | Griggs |
| 4,604,995 A | 8/1986 | Stephens et al. |
| 4,772,287 A | 9/1988 | Ray et al. |
| 4,877,020 A | 10/1989 | Vich |
| 4,878,915 A | 11/1989 | Brantigan |
| 5,015,247 A | 5/1991 | Michelson |
| 5,026,373 A | 6/1991 | Ray et al. |
| 5,100,405 A | 3/1992 | McLaren |
| 5,135,528 A | 8/1992 | Winston |
| 5,236,460 A | 8/1993 | Barber |
| 5,484,437 A | 1/1996 | Michelson |
| 5,489,307 A | 2/1996 | Kuslich et al. |
| 5,505,732 A | 4/1996 | Michelson |
| 5,527,312 A | 6/1996 | Ray |
| 5,549,679 A | 8/1996 | Kuslich et al. |
| 5,554,191 A | 9/1996 | Lahille et al. |
| 5,571,191 A | 11/1996 | Fitz |
| 5,584,832 A | 12/1996 | Schlapfer et al. |
| 5,593,409 A | 1/1997 | Michelson |
| 5,632,747 A | 5/1997 | Scarborough et al. |
| 5,649,945 A | 7/1997 | Ray et al. |
| 5,653,763 A | 8/1997 | Errico et al. |
| 5,665,122 A | 9/1997 | Kambin |
| 5,674,295 A | 10/1997 | Ray et al. |
| 5,720,748 A | 2/1998 | Kuslich et al. |
| 5,741,253 A | 4/1998 | Michelson |
| 5,772,661 A | 6/1998 | Michelson |
| 5,792,044 A | 8/1998 | Foley et al. |
| 5,797,909 A | 8/1998 | Michelson |
| 5,836,948 A | 11/1998 | Zucherman et al. |
| 5,879,353 A | 3/1999 | Terry |
| 5,885,299 A | 3/1999 | Winslow et al. |
| 5,891,147 A | 4/1999 | Moskovitz |
| 5,895,426 A | 4/1999 | Scarborough et al. |
| 5,899,908 A | 5/1999 | Kuslich et al. |
| 5,928,238 A | 7/1999 | Scarborough et al. |
| 5,953,820 A | 9/1999 | Vasudeva |
| 5,961,522 A | 10/1999 | Mehdizadeh |
| 5,976,146 A | 11/1999 | Ogawa et al. |
| 6,008,433 A | 12/1999 | Stone |
| 6,033,405 A | 3/2000 | Winslow et al. |
| 6,045,580 A | 4/2000 | Scarborough et al. |
| 6,063,088 A | 5/2000 | Winslow |
| RE36,758 E | 6/2000 | Fitz |
| 6,080,155 A | 6/2000 | Michelson |
| 6,090,143 A | 7/2000 | Meriwether et al. |
| 6,096,038 A | 8/2000 | Michelson |
| 6,099,531 A | 8/2000 | Bonutti |
| 6,102,950 A | 8/2000 | Vaccaro |
| 6,113,602 A | 9/2000 | Sand |
| 6,149,650 A | 11/2000 | Michelson |
| RE37,005 E | 12/2000 | Michelson et al. |
| 6,159,245 A | 12/2000 | Meriwether et al. |
| 6,176,882 B1 | 1/2001 | Biedermann et al. |
| 6,179,873 B1 | 1/2001 | Zientek |
| 6,190,388 B1 | 2/2001 | Michelson et al. |
| 6,190,414 B1 | 2/2001 | Young et al. |
| 6,193,757 B1 | 2/2001 | Foley et al. |
| 6,210,412 B1 | 4/2001 | Michelson |
| RE37,161 E | 5/2001 | Michelson et al. |
| 6,224,595 B1 | 5/2001 | Michelson |
| 6,224,607 B1 | 5/2001 | Michelson |
| 6,224,630 B1 | 5/2001 | Bao et al. |
| 6,245,108 B1 | 6/2001 | Biscup |
| 6,248,110 B1 | 6/2001 | Reiley et al. |
| D444,878 S | 7/2001 | Walter |
| D445,188 S | 7/2001 | Walter |
| 6,264,656 B1 | 7/2001 | Michelson |
| 6,267,763 B1 | 7/2001 | Castro |
| 6,270,498 B1 | 8/2001 | Michelson |
| 6,283,966 B1 | 9/2001 | Boufburg |
| 6,315,795 B1 | 11/2001 | Scarborough et al. |
| 6,325,827 B1 | 12/2001 | Lin |
| 6,371,984 B1 | 4/2002 | Van Dyke et al. |
| 6,371,988 B1 | 4/2002 | Pafford et al. |
| 6,402,784 B1 | 6/2002 | Wardlaw |
| 6,423,063 B1 | 7/2002 | Bonutti |
| 6,423,083 B2 | 7/2002 | Reiley et al. |
| 6,425,919 B1 | 7/2002 | Lambrecht |
| 6,436,098 B1 | 8/2002 | Michelson |
| 6,436,142 B1 | 8/2002 | Paes et al. |
| 6,443,988 B2 | 9/2002 | Felt et al. |
| 6,451,023 B1 | 9/2002 | Salazar et al. |
| 6,454,807 B1 | 9/2002 | Jackson |
| 6,478,796 B2 | 11/2002 | Zucherman et al. |
| 6,500,206 B1 | 12/2002 | Bryan |
| 6,514,256 B2 | 2/2003 | Zucherman et al. |
| 6,530,955 B2 | 3/2003 | Boyle et al. |
| 6,558,390 B2 | 5/2003 | Cragg |
| 6,565,574 B2 | 5/2003 | Michelson |
| 6,565,605 B2 | 5/2003 | Fallin et al. |
| 6,569,186 B1 | 5/2003 | Winters et al. |
| 6,575,919 B1 | 6/2003 | Reiley et al. |
| 6,575,979 B1 | 6/2003 | Cragg |
| 6,579,319 B2 | 6/2003 | Goble et al. |
| 6,582,432 B1 | 6/2003 | Michelson |
| 6,607,530 B1 | 8/2003 | Carl et al. |
| 6,610,091 B1 | 8/2003 | Reiley |
| 6,626,905 B1 | 9/2003 | Schmiel et al. |
| 6,632,235 B2 | 10/2003 | Weikel et al. |
| 6,635,060 B2 | 10/2003 | Hanson et al. |
| 6,641,582 B1 | 11/2003 | Hanson et al. |
| 6,648,893 B2 | 11/2003 | Dudasik |
| 6,652,584 B2 | 11/2003 | Michelson |
| 6,663,647 B2 | 12/2003 | Reiley et al. |
| 6,666,866 B2 | 12/2003 | Martz et al. |
| 6,679,886 B2 | 1/2004 | Weikel et al. |
| 6,682,535 B2 | 1/2004 | Hoogland |
| 6,685,742 B1 | 2/2004 | Jackson |
| 6,709,458 B2 | 3/2004 | Michelson |
| 6,712,853 B2 | 3/2004 | Kuslich |
| 6,719,773 B1 | 4/2004 | Boucher et al. |
| 6,723,095 B2 | 4/2004 | Hammerslag |
| 6,733,534 B2 | 5/2004 | Sherman |
| 6,740,093 B2 | 5/2004 | Hochschuler et al. |
| 6,751,875 B2 | 6/2004 | Jones |
| 6,770,074 B2 | 8/2004 | Michelson |
| 6,793,679 B2 | 9/2004 | Michelson |
| 6,805,715 B2 | 10/2004 | Reuter et al. |
| 6,808,537 B2 | 10/2004 | Michelson |
| 6,823,871 B2 | 11/2004 | Schmieding |
| 6,840,941 B2 | 1/2005 | Rogers et al. |
| 6,851,430 B2 | 2/2005 | Tsou |
| 6,875,213 B2 | 4/2005 | Michelson |
| 6,899,719 B2 | 5/2005 | Reiley et al. |
| 6,921,403 B2 | 7/2005 | Cragg et al. |
| 6,923,813 B2 | 8/2005 | Phillips et al. |
| 6,958,077 B2 | 10/2005 | Suddaby |
| 6,962,606 B2 | 11/2005 | Michelson |
| 6,964,686 B2 | 11/2005 | Gordon |
| 6,966,930 B2 | 11/2005 | Arnin et al. |
| 6,972,035 B2 | 12/2005 | Michelson |
| 6,974,478 B2 | 12/2005 | Reiley et al. |
| 6,979,333 B2 | 12/2005 | Hammerslag |
| 6,986,772 B2 | 1/2006 | Michelson |
| 7,001,385 B2 | 2/2006 | Bonutti |
| 7,008,453 B1 | 3/2006 | Michelson |
| 7,033,362 B2 | 4/2006 | McGahan et al. |
| 7,033,392 B2 | 4/2006 | Schmiel et al. |
| 7,033,394 B2 | 4/2006 | Michelson |
| 7,066,961 B2 | 6/2006 | Michelson |
| D524,443 S | 7/2006 | Blain |
| 7,083,623 B2 | 8/2006 | Michelson |
| 7,090,698 B2 | 8/2006 | Fallin et al. |
| 7,096,972 B2 | 8/2006 | Orozco, Jr. |
| 7,101,398 B2 | 9/2006 | Dooris et al. |

(56) References Cited

U.S. PATENT DOCUMENTS

| | | |
|---|---|---|
| 7,115,128 B2 | 10/2006 | Michelson |
| 7,118,598 B2 | 10/2006 | Michelson |
| 7,128,760 B2 | 10/2006 | Michelson |
| 7,156,877 B2 | 1/2007 | Lotz et al. |
| 7,166,110 B2 | 1/2007 | Yundt |
| 7,175,023 B2 | 2/2007 | Martin |
| 7,179,263 B2 | 2/2007 | Zdeblick et al. |
| 7,207,991 B2 | 4/2007 | Michelson |
| D541,940 S | 5/2007 | Blain |
| 7,220,280 B2 | 5/2007 | Kast et al. |
| 7,264,622 B2 | 9/2007 | Michelson |
| 7,273,498 B2 | 9/2007 | Bianchi et al. |
| 7,288,093 B2 | 10/2007 | Michelson |
| 7,291,149 B1 | 11/2007 | Michelson |
| 7,300,440 B2 | 11/2007 | Zdeblick et al. |
| 7,326,211 B2 | 2/2008 | Padget et al. |
| 7,326,214 B2 | 2/2008 | Michelson |
| 7,371,238 B2 | 5/2008 | Soboleski et al. |
| 7,399,303 B2 | 7/2008 | Michelson |
| 7,410,501 B2 | 8/2008 | Michelson |
| 7,431,722 B1 | 10/2008 | Michelson |
| 7,445,636 B2 | 11/2008 | Michelson |
| 7,452,359 B1 | 11/2008 | Michelson |
| 7,452,369 B2 | 11/2008 | Barry |
| 7,465,304 B1 | 12/2008 | Haufe et al. |
| 7,476,226 B2 | 1/2009 | Weikel et al. |
| 7,476,251 B2 | 1/2009 | Zucherman et al. |
| 7,479,160 B2 | 1/2009 | Branch et al. |
| 7,491,205 B1 | 2/2009 | Michelson |
| 7,500,992 B2 | 3/2009 | Li |
| 7,517,358 B2 | 4/2009 | Peterson |
| 7,524,333 B2 | 4/2009 | Lambrecht et al. |
| 7,569,054 B2 | 8/2009 | Michelson |
| 7,569,057 B2 | 8/2009 | Liu et al. |
| 7,580,743 B2 | 8/2009 | Bourlion et al. |
| 7,591,851 B2 | 9/2009 | Winslow et al. |
| 7,601,170 B2 | 10/2009 | Winslow et al. |
| 7,608,077 B2 | 10/2009 | Cragg et al. |
| 7,608,107 B2 | 10/2009 | Michelson |
| 7,615,079 B2 | 11/2009 | Flickinger et al. |
| 7,618,451 B2 | 11/2009 | Berez et al. |
| 7,632,291 B2 | 12/2009 | Stephens et al. |
| 7,641,664 B2 | 1/2010 | Pagano |
| 7,648,523 B2 | 1/2010 | Mirkovic et al. |
| 7,655,027 B2 | 2/2010 | Michelson |
| 7,655,043 B2 | 2/2010 | Peterman et al. |
| 7,662,173 B2 | 2/2010 | Cragg et al. |
| D611,147 S | 3/2010 | Hanson et al. |
| 7,682,378 B2 | 3/2010 | Truckai et al. |
| 7,686,805 B2 | 3/2010 | Michelson |
| 7,686,807 B2 | 3/2010 | Padget et al. |
| 7,699,878 B2 | 4/2010 | Pavlov et al. |
| D615,653 S | 5/2010 | Horton |
| 7,708,761 B2 | 5/2010 | Petersen |
| 7,722,619 B2 | 5/2010 | Michelson |
| D619,719 S | 7/2010 | Pannu |
| 7,763,024 B2 | 7/2010 | Bertagnoli et al. |
| 7,763,050 B2 | 7/2010 | Winslow et al. |
| 7,776,090 B2 | 8/2010 | Winslow et al. |
| D623,748 S | 9/2010 | Horton et al. |
| D623,749 S | 9/2010 | Horton et al. |
| 7,789,898 B2 | 9/2010 | Peterman |
| D627,468 S | 11/2010 | Richter et al. |
| 7,824,431 B2 | 11/2010 | McCormack |
| 7,837,713 B2 | 11/2010 | Peterson |
| 7,846,183 B2 | 12/2010 | Blain |
| 7,846,184 B2 | 12/2010 | Sasso et al. |
| 7,850,733 B2 | 12/2010 | Baynham et al. |
| 7,862,589 B2 | 1/2011 | Thramann |
| 7,867,277 B1 | 1/2011 | Tohmeh |
| D631,967 S | 2/2011 | Horton |
| 7,879,098 B1 | 2/2011 | Simmons, Jr. |
| 7,887,565 B2 | 2/2011 | Michelson |
| 7,892,261 B2 | 2/2011 | Bonutti |
| 7,892,286 B2 | 2/2011 | Michelson |
| 7,896,803 B2 | 3/2011 | Schara et al. |
| 7,896,903 B2 | 3/2011 | Link |
| 7,901,439 B2 | 3/2011 | Horton |
| 7,914,530 B2 | 3/2011 | Michelson |
| 7,918,891 B1 | 4/2011 | Curran et al. |
| 7,922,729 B2 | 4/2011 | Michelson |
| 7,922,766 B2 | 4/2011 | Grob et al. |
| 7,935,136 B2 | 5/2011 | Alamin et al. |
| 7,938,857 B2 | 5/2011 | Krueger et al. |
| 7,988,712 B2 | 8/2011 | Hale et al. |
| 7,988,714 B2 | 8/2011 | Puekert et al. |
| 7,998,174 B2 | 8/2011 | Malandain et al. |
| 8,007,534 B2 | 8/2011 | Michelson |
| 8,029,540 B2 | 10/2011 | Winslow et al. |
| 8,043,334 B2 | 10/2011 | Fisher et al. |
| 8,052,728 B2 | 11/2011 | Hestad |
| 8,062,303 B2 | 11/2011 | Berry et al. |
| 8,066,705 B2 | 11/2011 | Michelson |
| D650,481 S | 12/2011 | Gottlieb et al. |
| 8,097,034 B2 | 1/2012 | Michelson |
| 8,100,944 B2 | 1/2012 | Lauryssen et al. |
| D653,757 S | 2/2012 | Binder |
| 8,114,158 B2 | 2/2012 | Carl et al. |
| 8,118,838 B2 | 2/2012 | Winslow et al. |
| 8,128,660 B2 | 3/2012 | Mitchel et al. |
| 8,133,261 B2 | 3/2012 | Fisher et al. |
| 8,142,503 B2 | 3/2012 | Malone |
| 8,147,553 B2 | 4/2012 | Vresilovic et al. |
| 8,162,981 B2 | 4/2012 | Vestgaarden |
| 8,172,877 B2 | 5/2012 | Winslow et al. |
| 8,177,872 B2 | 5/2012 | Nelson et al. |
| 8,197,513 B2 | 6/2012 | Fisher et al. |
| 8,206,418 B2 | 6/2012 | Triplett et al. |
| 8,267,966 B2 | 9/2012 | McCormack et al. |
| D674,900 S | 1/2013 | Janice et al. |
| 8,348,979 B2 | 1/2013 | McCormack |
| 8,361,152 B2 | 1/2013 | McCormack et al. |
| 8,366,748 B2 | 2/2013 | Kleiner |
| D677,791 S | 3/2013 | Danacioglu et al. |
| 8,394,107 B2 | 3/2013 | Fanger et al. |
| 8,394,129 B2 | 3/2013 | Morgenstern et al. |
| D681,205 S | 4/2013 | Farris et al. |
| 8,425,558 B2 | 4/2013 | McCormack et al. |
| 8,512,347 B2 | 8/2013 | McCormack et al. |
| 8,523,908 B2 | 9/2013 | Malone |
| 8,623,054 B2 | 1/2014 | McCormack et al. |
| 8,668,722 B2 | 3/2014 | Pavlov et al. |
| 8,753,347 B2 | 6/2014 | McCormack et al. |
| 8,764,755 B2 | 7/2014 | Michelson |
| 8,828,062 B2 | 9/2014 | McCormack et al. |
| 8,834,530 B2 | 9/2014 | McCormack |
| 8,845,727 B2 | 9/2014 | Gottlieb et al. |
| 8,870,882 B2 | 10/2014 | Kleiner |
| D723,690 S | 3/2015 | McCormack et al. |
| D723,691 S | 3/2015 | McCormack et al. |
| 8,998,905 B2 | 4/2015 | Marik et al. |
| 9,011,492 B2 | 4/2015 | McCormack et al. |
| D732,667 S | 6/2015 | McCormack et al. |
| D745,156 S | 12/2015 | McCormack et al. |
| 9,211,198 B2 | 12/2015 | Michelson |
| 9,220,608 B2 | 12/2015 | McKay |
| D750,249 S | 2/2016 | Grimberg, Jr. et al. |
| 9,271,765 B2 | 3/2016 | Blain |
| 9,333,086 B2 | 5/2016 | McCormack et al. |
| 9,381,049 B2 | 7/2016 | McCormack et al. |
| 9,427,264 B2 | 8/2016 | Kleiner et al. |
| 9,504,583 B2 | 11/2016 | Blain |
| 9,717,403 B2 | 8/2017 | Kleiner et al. |
| 2001/0004710 A1 | 6/2001 | Felt et al. |
| 2001/0047208 A1 | 11/2001 | Michelson |
| 2002/0026195 A1 | 2/2002 | Layne et al. |
| 2002/0107519 A1 | 8/2002 | Dixon et al. |
| 2002/0143343 A1 | 10/2002 | Castro |
| 2002/0147496 A1 | 10/2002 | Belef et al. |
| 2002/0147497 A1 | 10/2002 | Belef et al. |
| 2002/0165612 A1 | 11/2002 | Gerber et al. |
| 2002/0169471 A1 | 11/2002 | Ferdinand |
| 2003/0023312 A1 | 1/2003 | Thalgott |
| 2003/0028251 A1 | 2/2003 | Mathews |

(56) References Cited

U.S. PATENT DOCUMENTS

| | | |
|---|---|---|
| 2003/0032962 A1 | 2/2003 | McGahan et al. |
| 2003/0033017 A1 | 2/2003 | Lotz et al. |
| 2003/0105526 A1 | 6/2003 | Bryant et al. |
| 2003/0109928 A1 | 6/2003 | Pasquet et al. |
| 2003/0139816 A1 | 7/2003 | Michelson |
| 2003/0144737 A1 | 7/2003 | Sherman |
| 2003/0158553 A1 | 8/2003 | Michelson |
| 2003/0225416 A1 | 12/2003 | Bonvallet et al. |
| 2004/0059337 A1 | 3/2004 | Hanson et al. |
| 2004/0073217 A1 | 4/2004 | Michelson |
| 2004/0087948 A1 | 5/2004 | Suddaby |
| 2004/0087956 A1 | 5/2004 | Weikel et al. |
| 2004/0106999 A1 | 6/2004 | Mathews |
| 2004/0133277 A1 | 7/2004 | Michelson |
| 2004/0133280 A1 | 7/2004 | Trieu |
| 2004/0162562 A1 | 8/2004 | Martz |
| 2004/0215344 A1 | 10/2004 | Hochshculer et al. |
| 2005/0010294 A1 | 1/2005 | Michelson |
| 2005/0015149 A1 | 1/2005 | Michelson |
| 2005/0027358 A1 | 2/2005 | Suddaby |
| 2005/0033432 A1 | 2/2005 | Gordon et al. |
| 2005/0049705 A1 | 3/2005 | Hale et al. |
| 2005/0055096 A1 | 3/2005 | Serhan et al. |
| 2005/0065518 A1 | 3/2005 | Michelson |
| 2005/0065519 A1 | 3/2005 | Michelson |
| 2005/0065608 A1 | 3/2005 | Michelson |
| 2005/0065609 A1 | 3/2005 | Wardlaw |
| 2005/0080422 A1 | 4/2005 | Otte et al. |
| 2005/0090829 A1 | 4/2005 | Martz et al. |
| 2005/0090901 A1 | 4/2005 | Studer |
| 2005/0119680 A1 | 6/2005 | Dykes |
| 2005/0124993 A1 | 6/2005 | Chappuis |
| 2005/0159650 A1 | 7/2005 | Raymond et al. |
| 2005/0159746 A1 | 7/2005 | Grob et al. |
| 2005/0177240 A1 | 8/2005 | Blain |
| 2005/0182417 A1 | 8/2005 | Pagano |
| 2005/0216018 A1 | 9/2005 | Sennett |
| 2005/0240188 A1 | 10/2005 | Chow et al. |
| 2005/0251146 A1 | 11/2005 | Martz et al. |
| 2005/0251257 A1 | 11/2005 | Mitchell et al. |
| 2005/0267480 A1 | 12/2005 | Suddaby |
| 2006/0004367 A1 | 1/2006 | Alamin et al. |
| 2006/0015184 A1 | 1/2006 | Winterbottom et al. |
| 2006/0036243 A1 | 2/2006 | Sasso et al. |
| 2006/0036247 A1 | 2/2006 | Michelson |
| 2006/0036323 A1 | 2/2006 | Carl et al. |
| 2006/0041311 A1 | 2/2006 | McLeer |
| 2006/0058793 A1 | 3/2006 | Michelson |
| 2006/0058878 A1 | 3/2006 | Michelson |
| 2006/0069442 A1 | 3/2006 | Michelson |
| 2006/0079905 A1 | 4/2006 | Beyar et al. |
| 2006/0079962 A1 | 4/2006 | Michelson |
| 2006/0085068 A1 | 4/2006 | Barry |
| 2006/0085074 A1 | 4/2006 | Raiszadeh |
| 2006/0095028 A1 | 5/2006 | Bleich |
| 2006/0095036 A1 | 5/2006 | Hammerslag |
| 2006/0111779 A1 | 5/2006 | Petersen |
| 2006/0111780 A1 | 5/2006 | Petersen |
| 2006/0111781 A1 | 5/2006 | Petersen |
| 2006/0142762 A1 | 6/2006 | Michelson |
| 2006/0149289 A1 | 7/2006 | Winslow et al. |
| 2006/0184172 A1 | 8/2006 | Michelson |
| 2006/0190081 A1 | 8/2006 | Kraus et al. |
| 2006/0195109 A1 | 8/2006 | McGahan et al. |
| 2006/0200137 A1 | 9/2006 | Soboleski et al. |
| 2006/0200138 A1 | 9/2006 | Michelson |
| 2006/0200139 A1 | 9/2006 | Michelson |
| 2006/0206118 A1 | 9/2006 | Kim et al. |
| 2006/0217812 A1 | 9/2006 | Lambrecht et al. |
| 2006/0235391 A1 | 10/2006 | Sutterlin, III |
| 2006/0241597 A1 | 10/2006 | Mitchell et al. |
| 2006/0241626 A1 | 10/2006 | McGahan et al. |
| 2006/0241758 A1 | 10/2006 | Peterman et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0259142 A1 | 11/2006 | Dooris et al. |
| 2006/0271195 A1 | 11/2006 | Thramann |
| 2006/0276790 A1 | 12/2006 | Dawson et al. |
| 2006/0276801 A1 | 12/2006 | Yerby et al. |
| 2006/0276897 A1 | 12/2006 | Winslow et al. |
| 2006/0293663 A1 | 12/2006 | Walkenhorst et al. |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0032871 A1 | 2/2007 | Michelson |
| 2007/0043362 A1 | 2/2007 | Malandain et al. |
| 2007/0050031 A1 | 3/2007 | Khosrowshahi |
| 2007/0055245 A1 | 3/2007 | Sasso et al. |
| 2007/0055263 A1 | 3/2007 | Way et al. |
| 2007/0073402 A1 | 3/2007 | Vresilovic et al. |
| 2007/0083265 A1 | 4/2007 | Malone |
| 2007/0123863 A1 | 5/2007 | Winslow et al. |
| 2007/0123888 A1 | 5/2007 | Bleich et al. |
| 2007/0135814 A1 | 6/2007 | Farris |
| 2007/0135921 A1 | 6/2007 | Park |
| 2007/0149976 A1 | 6/2007 | Hale et al. |
| 2007/0149983 A1 | 6/2007 | Link |
| 2007/0150061 A1 | 6/2007 | Trieu |
| 2007/0161991 A1 | 7/2007 | Altarac et al. |
| 2007/0179617 A1 | 8/2007 | Brown et al. |
| 2007/0179619 A1 | 8/2007 | Grob et al. |
| 2007/0225721 A1 | 9/2007 | Thelen et al. |
| 2007/0225812 A1 | 9/2007 | Gill |
| 2007/0244483 A9 | 10/2007 | Winslow et al. |
| 2007/0276491 A1 | 11/2007 | Ahrens |
| 2007/0282441 A1 | 12/2007 | Stream et al. |
| 2007/0288014 A1 | 12/2007 | Shadduck et al. |
| 2007/0299451 A1 | 12/2007 | Tulkis |
| 2008/0015581 A1 | 1/2008 | Eckman |
| 2008/0021457 A1 | 1/2008 | Anderson et al. |
| 2008/0021464 A1 | 1/2008 | Morin et al. |
| 2008/0045970 A1 | 2/2008 | Saidha et al. |
| 2008/0058954 A1 | 3/2008 | Trieu |
| 2008/0065219 A1 | 3/2008 | Dye |
| 2008/0097436 A1 | 4/2008 | Culbert et al. |
| 2008/0108996 A1 | 5/2008 | Padget et al. |
| 2008/0140207 A1 | 6/2008 | Olmos et al. |
| 2008/0161810 A1 | 7/2008 | Melkent |
| 2008/0161929 A1 | 7/2008 | McCormack et al. |
| 2008/0167657 A1 | 7/2008 | Greenhalgh |
| 2008/0177311 A1 | 7/2008 | Winslow et al. |
| 2008/0208341 A1 | 8/2008 | McCormack et al. |
| 2008/0216846 A1 | 9/2008 | Levin |
| 2008/0234677 A1 | 9/2008 | Dahners et al. |
| 2008/0234758 A1 | 9/2008 | Fisher et al. |
| 2008/0255564 A1 | 10/2008 | Michelson |
| 2008/0255618 A1 | 10/2008 | Fisher et al. |
| 2008/0255622 A1 | 10/2008 | Mickiewicz et al. |
| 2008/0255666 A1 | 10/2008 | Fisher et al. |
| 2008/0255667 A1 | 10/2008 | Horton |
| 2008/0287955 A1 | 11/2008 | Michelson |
| 2008/0306537 A1 | 12/2008 | Culbert |
| 2008/0312744 A1 | 12/2008 | Vresilovic et al. |
| 2009/0131986 A1 | 5/2009 | Lee et al. |
| 2009/0138053 A1 | 5/2009 | Assell et al. |
| 2009/0177205 A1 | 7/2009 | McCormack et al. |
| 2009/0177237 A1 | 7/2009 | Zucherman et al. |
| 2009/0234397 A1 | 9/2009 | Petersen |
| 2009/0248076 A1 | 10/2009 | Reynolds et al. |
| 2009/0263461 A1 | 10/2009 | McKay |
| 2009/0270929 A1 | 10/2009 | Suddaby et al. |
| 2009/0275994 A1 | 11/2009 | Phan et al. |
| 2009/0306671 A1 | 12/2009 | McCormack et al. |
| 2009/0312763 A1 | 12/2009 | McCormack et al. |
| 2010/0069912 A1 | 3/2010 | McCormack et al. |
| 2010/0086185 A1 | 4/2010 | Weiss |
| 2010/0093829 A1 | 4/2010 | Gorman |
| 2010/0111829 A1 | 5/2010 | Drapeau et al. |
| 2010/0114105 A1 | 5/2010 | Butters et al. |
| 2010/0114318 A1* | 5/2010 | Gittings ............... A61F 2/442 623/17.12 |
| 2010/0145391 A1 | 6/2010 | Kleiner |
| 2010/0191241 A1 | 7/2010 | McCormack et al. |

(56) References Cited

U.S. PATENT DOCUMENTS

| | | |
|---|---|---|
| 2011/0004247 A1 | 1/2011 | Lechmann et al. |
| 2011/0022089 A1 | 1/2011 | Assell et al. |
| 2011/0054613 A1 | 3/2011 | Hansen |
| 2011/0077686 A1 | 3/2011 | Mishra et al. |
| 2011/0082548 A1 | 4/2011 | Assell et al. |
| 2011/0144755 A1 | 6/2011 | Baynham et al. |
| 2011/0190821 A1 | 8/2011 | Chin et al. |
| 2011/0245930 A1 | 10/2011 | Alley et al. |
| 2011/0295327 A1 | 12/2011 | Moskowitz et al. |
| 2011/0307061 A1 | 12/2011 | Assell et al. |
| 2012/0010659 A1* | 1/2012 | Angert ............... A61B 17/1757 606/247 |
| 2012/0010662 A1 | 1/2012 | O'Neil et al. |
| 2012/0010669 A1 | 1/2012 | O'Neil et al. |
| 2012/0065613 A1 | 3/2012 | Pepper et al. |
| 2012/0143334 A1 | 6/2012 | Boyce et al. |
| 2012/0215259 A1* | 8/2012 | Cannestra .......... A61B 17/7064 606/247 |
| 2012/0226358 A1 | 9/2012 | Kleiner |
| 2012/0265250 A1 | 10/2012 | Ali |
| 2012/0283776 A1 | 11/2012 | Mishra |
| 2012/0323242 A1 | 12/2012 | Tsuang et al. |
| 2013/0006364 A1 | 1/2013 | McCormack et al. |
| 2013/0012994 A1 | 1/2013 | McCormack et al. |
| 2013/0013070 A1 | 1/2013 | McCormack et al. |
| 2013/0018474 A1 | 1/2013 | McCormack et al. |
| 2013/0023995 A1 | 1/2013 | McCormack et al. |
| 2013/0023996 A1 | 1/2013 | McCormack et al. |
| 2013/0030440 A1 | 1/2013 | McCormack et al. |
| 2013/0030532 A1 | 1/2013 | McCormack et al. |
| 2013/0110168 A1 | 5/2013 | McCormack et al. |
| 2013/0110243 A1 | 5/2013 | Patterson et al. |
| 2013/0123922 A1 | 5/2013 | McCormack et al. |
| 2013/0144389 A1 | 6/2013 | Bonutti |
| 2013/0226239 A1 | 8/2013 | Altarac et al. |
| 2013/0253649 A1 | 9/2013 | Davis |
| 2013/0274763 A1 | 10/2013 | Drapeau et al. |
| 2013/0310839 A1 | 11/2013 | McCormack et al. |
| 2013/0310878 A1 | 11/2013 | McCormack et al. |
| 2013/0310943 A1 | 11/2013 | McCormack et al. |
| 2013/0317548 A1 | 11/2013 | Malone |
| 2013/0338720 A1 | 12/2013 | Kleiner |
| 2014/0025113 A1 | 1/2014 | McCormack et al. |
| 2014/0100657 A1 | 4/2014 | McCormack et al. |
| 2014/0379087 A1 | 12/2014 | McCormack |
| 2015/0297357 A1 | 10/2015 | McCormack et al. |
| 2017/0027713 A1 | 2/2017 | Kleiner |
| 2017/0189199 A1 | 7/2017 | Maier et al. |
| 2017/0216044 A1 | 8/2017 | McCormack |

FOREIGN PATENT DOCUMENTS

| | | |
|---|---|---|
| WO | 9641582 A1 | 12/1996 |
| WO | 99/49818 A1 | 10/1999 |
| WO | 00/35388 A1 | 6/2000 |
| WO | 00/53126 A1 | 9/2000 |
| WO | 0053126 A1 | 9/2000 |
| WO | 01/01895 A1 | 1/2001 |
| WO | 02/34120 A2 | 5/2002 |
| WO | 02/38062 A2 | 5/2002 |
| WO | 0234120 A2 | 5/2002 |
| WO | 02/076335 A2 | 10/2002 |
| WO | 2006058221 A2 | 6/2006 |
| WO | 2006130791 A2 | 12/2006 |
| WO | 2007120903 A2 | 10/2007 |
| WO | 2008083349 A1 | 7/2008 |
| WO | 2008153732 A1 | 12/2008 |
| WO | 2009089367 A2 | 7/2009 |
| WO | 2009148619 A2 | 12/2009 |
| WO | 2010030994 | 3/2010 |
| WO | 2010074714 | 7/2010 |
| WO | 20160049784 | 4/2016 |

OTHER PUBLICATIONS

Goel, Atul, "Facetal distraction as treatment for single- and multi-level cervical spondylotic radiculopathy and myelopathy: a preliminary report," J Neurosurg Spine, Jun. 2011, pp. 689-696.

Press Release, Interventional Spine, Inc., Interventional Spine, Inc. Introduces the PERPOS Fusion Facet Prep Kit, Oct. 14, 2008, 1 Page.

Press Release, minSURG Corp., Orthopedic Development Corporation's TruFUSE Procedure Tops 1,750 Patients in First Year, Sep. 24, 2007, 1 Page.

Press Release, Interventional Spine, Inc., FDA Grants Conditional Approval to Interventional Spine's PercuDyn System IDE Application, Jul. 1, 2008, 1 Page.

Stein et al., "Percutaneous Facet Joint Fusion: Preliminary Experience," Journal of Vascular and Interventional Radiology, Jan.-Feb. 1993, pp. 69-74, vol. 4, No. 1.

\* cited by examiner

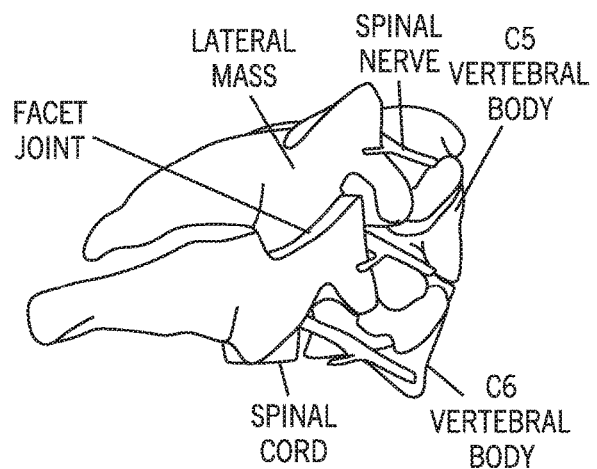
FIG. 1
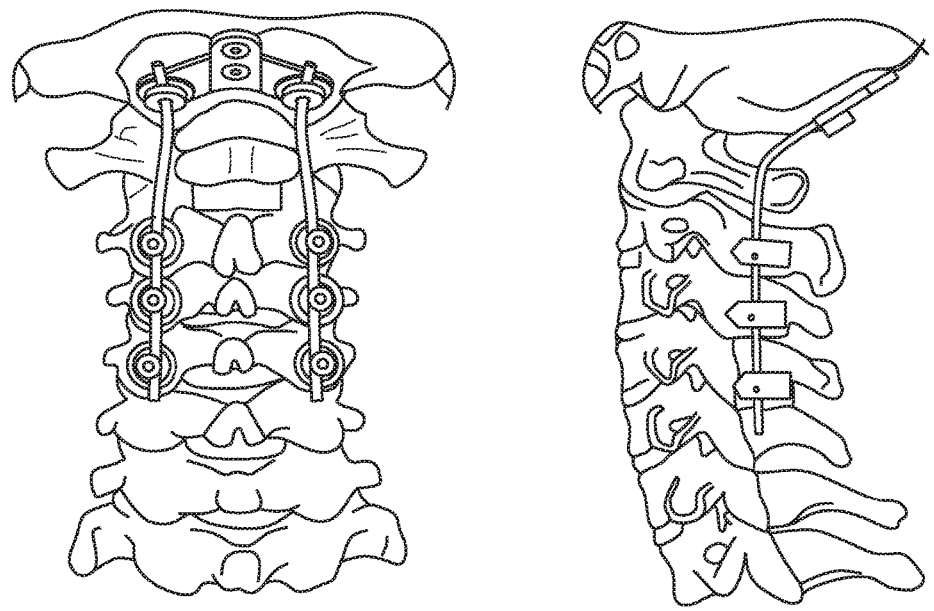
FIG. 2A
FIG. 2B

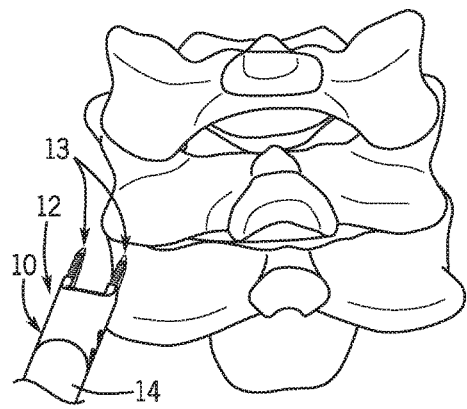 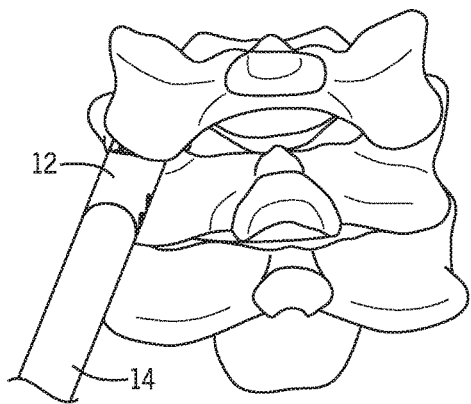
FIG. 3A　　　　　　FIG. 3B
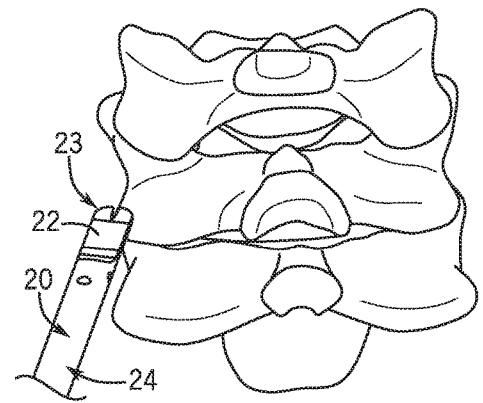 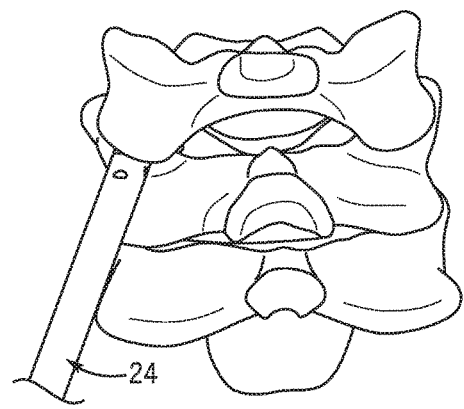
FIG. 4A　　　　　　FIG. 4B

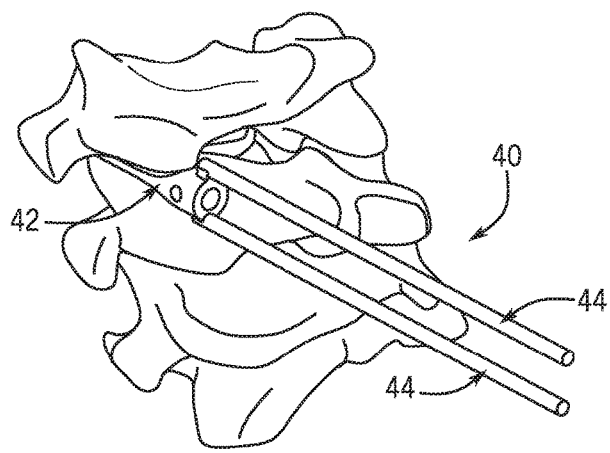
FIG. 8A
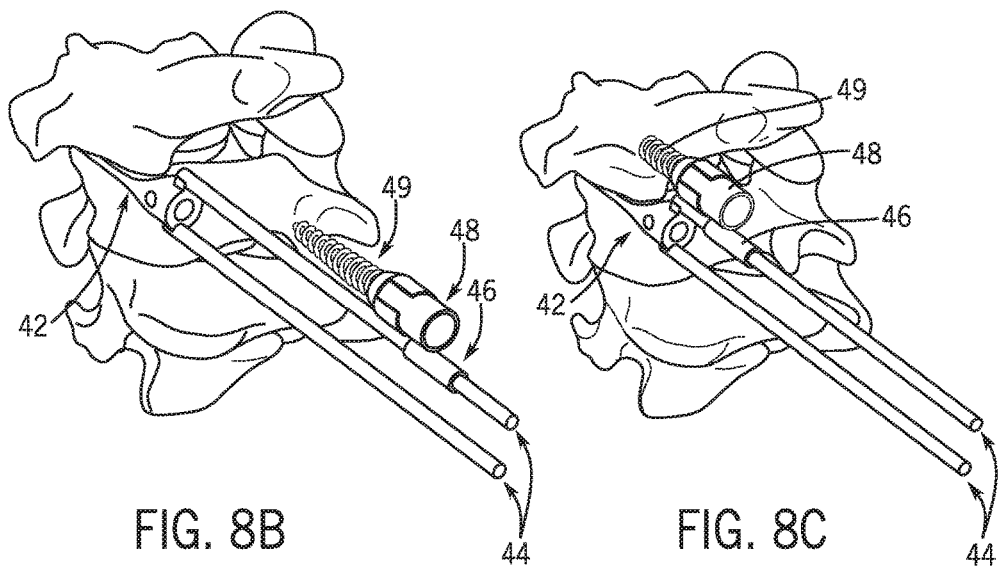
FIG. 8B
FIG. 8C

LATERAL MASS FIXATION SYSTEM

CROSS-REFERENCE TO RELATED APPLICATIONS

This application claims priority to U.S. Provisional Patent Application No. 62/004,143, entitled "Lateral Mass Fixation System," filed on May 28, 2014. The full disclosure of the above-listed patent application is hereby incorporated by reference herein.

BACKGROUND

Posterior cervical fusion with lateral mass fixation is the most rigid cervical instrumentation. It requires extensive dissection of muscles and ligaments off the posterior spine, so that the surgeon can have direct visualization to safely perform the procedure. This dissection causes acute and chronic soft tissue pain syndrome. Acutely, patients are typically hospitalized for three to four days for pain control that requires IV narcotics. This is compared to one-day hospitalization for anterior approaches that do not require any muscle or soft tissue dissection. Long-term patients with posterior approaches frequently have persistent pain due to the extensive nature of the dissection. Sometimes, after posterior-access cervical fusion surgery, soft tissues may not return to anatomic position and may be permanently deformed. Persistent pain after posterior surgical approaches is referred to as post-laminectomy syndrome. (FIG. 1 is a lateral view of the C5 and C6 cervical vertebrae, illustrating the anatomy.)

Therefore, since it is considered less traumatic to the patient compared to posterior approaches, anterior cervical spinal fusion surgery has generally been preferred over posterior fusion surgery. At the same time, posterior approaches to the cervical spine do have some advantages over anterior approaches.

Lateral mass or pedicle screw fixation provides more rigid fixation of the cervical spine than anterior plates, interbody devices and interspinous wiring. It is best for traumatic instability, but it has also been used for degenerative conditions. Despite being the best fixation, lateral mass fixation is often avoided, because of the morbidity of the soft tissue dissection, as noted above. (FIGS. 2A and 2B are posterior and lateral views, respectively, of a cervical spine with posterior fixation devices applied thereto.)

Starting a drill hole or inserting a screw into a lateral mass of a vertebra cannot currently be accomplished using a percutaneous approach. This is because soft tissue gets caught up in the drill, and the drill can skid off the bone and go out of control. Awls and firm pressure placed on bone with screws without direct visualization is dangerous in the posterior cervical spine, unless the surgeon has removed soft tissue and has direct visualization.

Therefore, it would be advantageous to have improved devices, systems and methods for performing cervical spinal fusion procedures via posterior access approaches. Ideally, these devices, systems and methods would allow for minimally invasive or less invasive access and fixation, as well as helping ensure proper placement of the fixation devices. At least some of these objectives will be met by the embodiments described herein.

BRIEF SUMMARY

The various embodiments described herein provide devices, systems and methods for accessing the cervical spine via a posterior approach and implanting a spinal fixation device in the cervical spine. The embodiments described below generally include a guide device, through which or along which one or more spinal fixation devices may be advanced. The guide devices described herein generally include a distal end that can be inserted into a cervical facet. Once inserted into a facet, the guide device is relatively stabilized (or "docked") on the spine and thus can be used as a point of stabilization.

A device for accessing and guiding at least one fixation device to a spine is disclosed. In some aspects, the device includes a distal portion configured to fit in a facet of the spine and a proximal portion extending from the distal portion. In various embodiments, the distal and proximal portions are hollow. In some embodiments, the distal and proximal portions are solid. The distal portion may be removable from the proximal portion. In some embodiments, the distal portion includes a chamfered or beveled end portion configured to facilitate insertion of the distal portion in the facet of the spine. The proximal portion may include a slot formed therethrough for receiving and advancing a fixation device to the spine. The end of the proximal portion may include opposing sides having a concave shape and/or opposing sides having a convex shape.

A system for accessing and guiding at least one fixation device to a spine is disclosed. In one aspect, the system includes a facet guide device, the facet guide device including a distal portion configured to fit in a facet of the spine and a proximal portion extending from the distal portion. The system further includes a slidable guide device for sliding over the facet guide device to guide at least one instrument to the spine. The slidable guide device may be rotatable about a longitudinal axis of the facet guide device. The instrument may be a decortication device. The slidable guide device may be a double-barreled or dual-lumen guide tube. The slidable guide device may further include a drill guide having at least one drill path defined therein. The proximal portion of the facet guide device may have one of a circular cross-sectional shape or a square cross-sectional shape. The proximal portion of the facet guide device may have opposing sides having a concave shape. The proximal portion of the facet guide device may have opposing sides having a convex shape. The slidable guide device may include a first tube for sliding over the proximal portion of the facet guide device and a second tube mounted on a side of the first tube for guiding the at least one instrument. The system may further include at least one bone screw for advancing through the slideable guide device.

A method for implanting a spinal fixation implant is disclosed. The method includes advancing a guide device into a facet between two adjacent vertebrae, advancing a fixation device along the guide device, and attaching the fixation device to at least one of the two adjacent vertebrae. The method may further include attaching the fixation device by one of attaching a plate to a facet implant located in the facet or attaching a plate to the two adjacent vertebrae.

These and other aspects and embodiments will be described in further detail below, in reference to the attached drawing figures.

BRIEF DESCRIPTION OF DRAWINGS

FIG. 1 is a lateral view of the C5 and C6 cervical vertebrae, illustrating the anatomy.

FIGS. 2A and 2B are posterior and lateral views, respectively, of a cervical spine with prior art posterior fixation devices applied thereto.

FIGS. 3A and 3B are posterior views of a portion of a cervical spine, illustrating insertion of a distal portion of a guide device into a facet between two cervical vertebrae, according to one embodiment.

FIGS. 4A and 4B are posterior views of a portion of a cervical spine, illustrating insertion of a distal portion of a guide device into a facet between two cervical vertebrae, according to an embodiment.

FIGS. 8A-8E are various views of a portion of a cervical spine, illustrating a system and method for inserting a lateral mass implant, according to an embodiment.

DETAILED DESCRIPTION

Figure 5A:
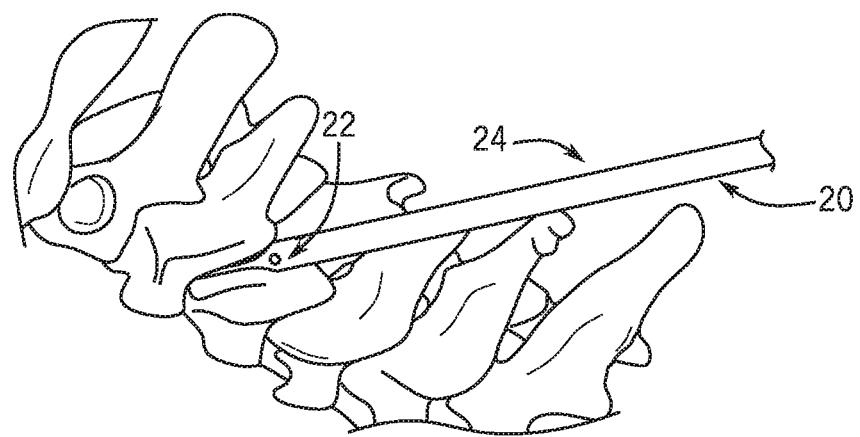
FIGS. 5A and 5B are lateral views of a portion of a cervical spine, illustrating insertion of a distal portion of a guide device into a facet between two cervical vertebrae and removal of a proximal portion of the guide device from the distal portion, according to one embodiment.

The various embodiments described herein provide devices, systems and methods for accessing the cervical spine via a posterior approach and implanting a spinal fixation device in the cervical spine. The embodiments allow for a posterior approach using minimally invasive or less invasive techniques. The embodiments described below generally include a guide tool, through which or along which one or more spinal fixation devices may be advanced.

The surgeon may advance the guide tool into the facet from outside the patient though a minimally invasive or less invasive incision, and then may hold the guide tool via a handle or proximal end residing outside the patient. This fixed point deep in the spine can be used to advance drills, awls, plates, rods and screws, to instrument the posterior cervical spine other than the facet, from a percutaneous approach without direct visualization. This avoids stripping all the soft tissue off the spine. A fixed point deep in the patient's spine prevents instruments from slipping off the spine or drills catching soft tissue and skidding out of control. Also, the cervical facet has a fixed anatomic relationship to lateral mass bone consistent in all patients. Instruments can be advanced over the facet tool to reliable landmarks on the lateral mass without direct visualization.

Some of the devices, systems and methods described herein may include, be performed using, or be similar to one or more components of the DTRAX® Spinal System, from Providence Medical Technology, Inc. (www.providencemt-.com). Various components of the DTRAX® Spinal System may be modified or adjusted, according to various embodiments, for uses described herein.

Referring now to FIGS. 3A and 3B, in one embodiment, a facet guide tool or device 10 may include a distal portion 12 configured for insertion into a facet space between two cervical vertebrae and a proximal portion 14 (or "shaft") that extends proximally from the distal portion 12. The proximal shaft portion 14 is generally long enough to extend from the distal portion 12 to a location outside the patient, where it can be held and manipulated by the surgeon. In one embodiment, the distal portion 12 may include two tines 13. In various embodiments, the distal portion 12 and the proximal portion 14 may either be two attached pieces or may be one piece (e.g. monolithically formed or integrally formed). In some embodiments, the two attached pieces may be detachable, as will be described further below. In some embodiments, the distal portion 12 may be temporary and may be removed once lateral mass fixation is achieved. The distal portion 12 is generally sized and shaped to fit snugly into the facet and abut the pedicle. The tight fit of distal portion 12 in the facet, due to forces applied by ligaments surrounding the area, helps provide stability to the facet guide tool 10 while fixation devices are advanced to the site.

In the embodiment of FIGS. 3A and 3B, the distal portion 12 and proximal portion 14 are hollow, thus forming a central lumen or bore (not visible in the figures), through which one or more facet fixation devices may be advanced. Alternatively or additionally, one or more fixation devices may be advanced over the guide tool 10 to the cervical spine. For example, a fixation device may have a hole formed therethrough of complementary size and shape to the guide tool 10. The hole may be aligned with the guide tool 10 and the fixation device may be advanced along the guide tool.

With reference to FIGS. 4A and 4B, in another embodiment, a facet guide tool or device 20 may include a distal portion 22 and a proximal portion 24. The distal portion 22 may include a beveled edge 23 to aid insertion of the distal portion into a facet. The distal portion 22 and the proximal portion 24 may both be solid, rather than hollow. In this embodiment, the guide tool 20 acts as a rail, over which one or more fixation devices or other devices may be advanced. In use, the guide tool 20 may be inserted in one facet or in multiple facets during a procedure. If used in multiple facets, multiple guide tools 20 may be inserted simultaneously, or the same guide tool may be inserted sequentially into multiple facets, to implant lateral mass or pedicle screw spinal instrumentation from a percutaneous approach. According to various alternative embodiments, the proximal shaft portion 24 may be flexible or rigid. Its purpose is to extend to the skin surface and serve as a guide for drills, plates, rods, screws and/or other tools of spinal instrumentation.

Figure 5B:
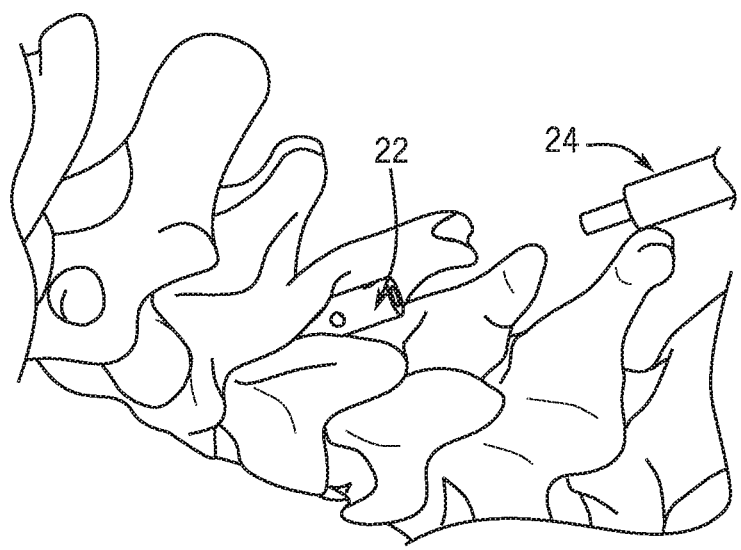

Referring now to FIGS. 5A and 5B, in some embodiments, the distal portion 22 of the guide tool or device 20 may be removable from the proximal portion 24, so that the distal portion 22 may be left in the facet as an implant. In some embodiments, one or more lateral mass fixation devices may then be attached to the distal portion 22 for contacting and attaching to lateral masses of adjacent vertebrae.

Figure 6A:
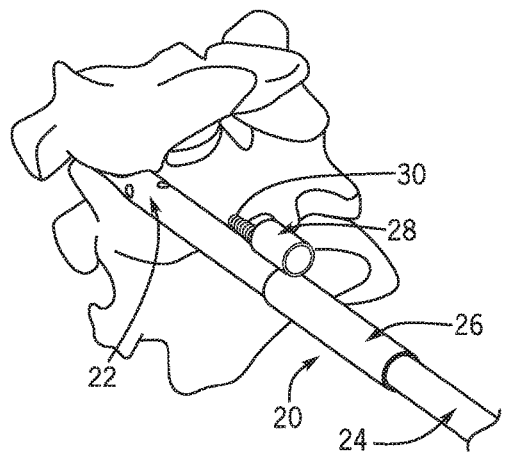
FIGS. 6A-6D are perspective views of a portion of a cervical spine, illustrating a system and method for inserting a lateral mass implant, according to one embodiment.
Figure 6B:
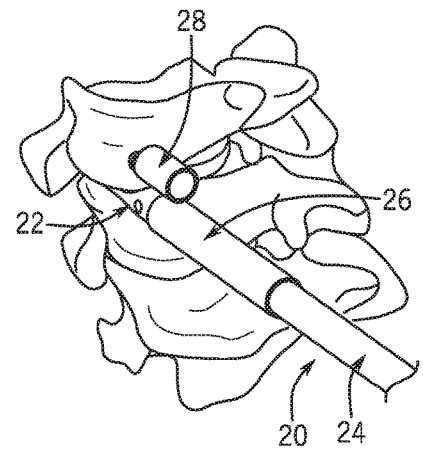
Figure 6C:
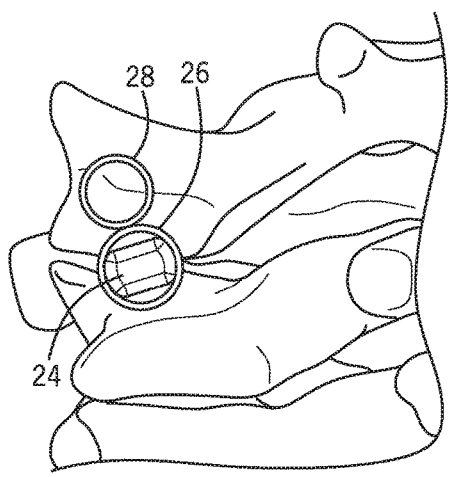
Figure 6D:
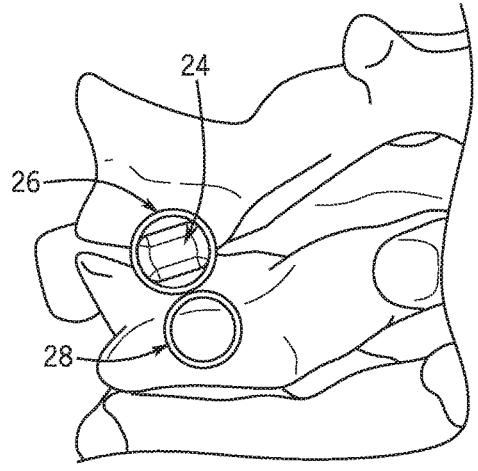

With reference to FIGS. 6A-6D, in one embodiment, a system for accessing and attaching fixation devices to a cervical spine facet may include the guide tool or device 20 with distal portion 22 and proximal portion 24, as described above. The system may also include an outer, sliding guide tube 26 and a side-mounted guide member 28 attached to the guide tube 26. A screw 30 may be advanced through the side-mounted guide member 28 for attachment to bone. As illustrated in FIGS. 6C and 6D, sliding guide tube 26 may be rotated about the proximal portion 24 of the guide device 20, to change the position of the side-mounted guide member 28. This change of position may be used, for example, to attach two screws to two adjacent vertebrae. The proximal portion 24 may have different cross-sectional shapes in different embodiments, with the circular cross-sectional shape providing 360-degree rotation of instruments advanced over it.

Figure 7A:
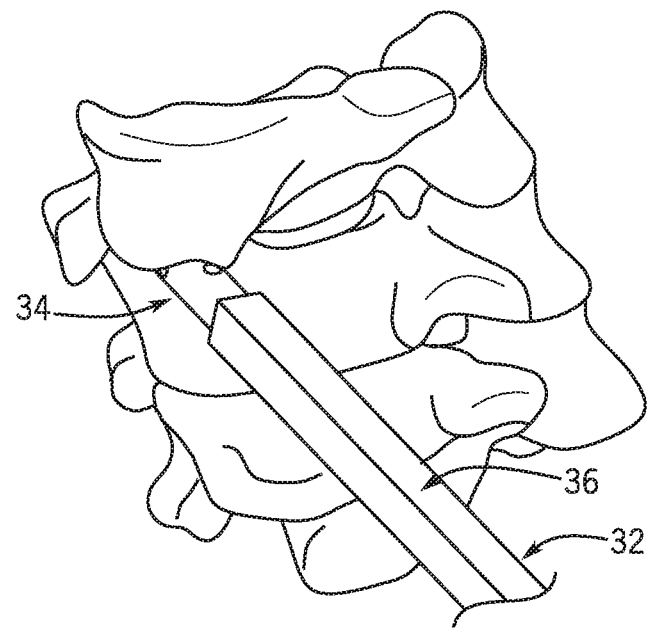
FIGS. 7A and 7B are perspective views of a portion of a cervical spine, illustrating a system and method for inserting a lateral mass implant, according to an embodiment.
Figure 7B:
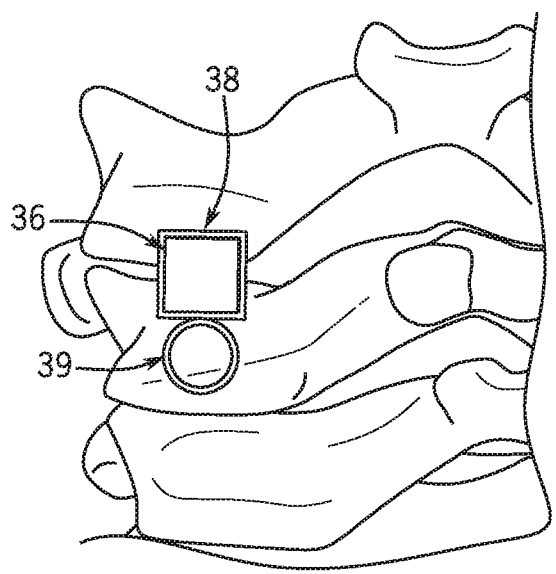

Referring to FIGS. 7A and 7B, in an alternative embodiment, a facet guide tool or device 32 may include a distal portion 34 and a proximal shaft portion 36 having a square cross-sectional shape. As illustrated in FIG. 7B, an additional guide device 38 may be advanced over the proximal portion 36 and may include a side-mounted guide tube 39. In this embodiment, the square cross-sectional shape of the proximal portion 36 allows instruments to be advanced at a fixed 90 degree angle to the facet surface. This may be useful for lateral mass fixation, because the typical screw fixation is at the midpoint of the lateral mass, which is immediately above the midpoint of the facet.

Figure 8D:
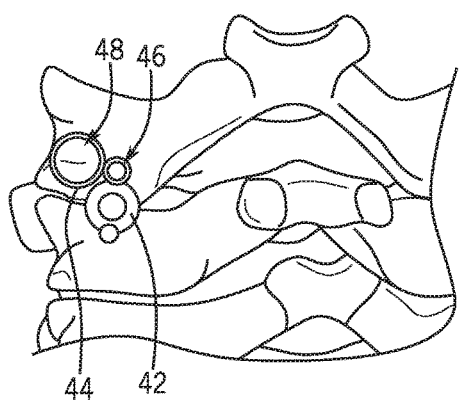
Figure 8E:
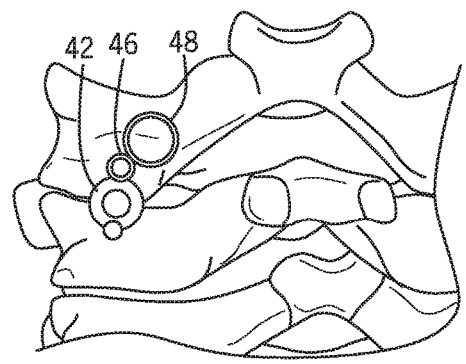

In yet another embodiment, and with reference now to FIGS. 8A-8E, a facet guide tool 40 may include a distal portion 42 and two or more proximal shafts 44. A guide system may further include a slidable guide instrument 46, with a side-mounted guide 48, which may be used to advance a screw 49 into bone. The proximal shafts 44 may be advantageous, for example, in advancing multiple guide instruments 46 to the cervical spine, either simultaneously or sequentially, for attaching screws to adjacent vertebrae. As illustrated in FIGS. 8D and 8E, the guide instrument 46 may also be rotated over one of the proximal shafts 44 to change the position of the side-mounted guide 48 relative to bone.

Figure 9A:
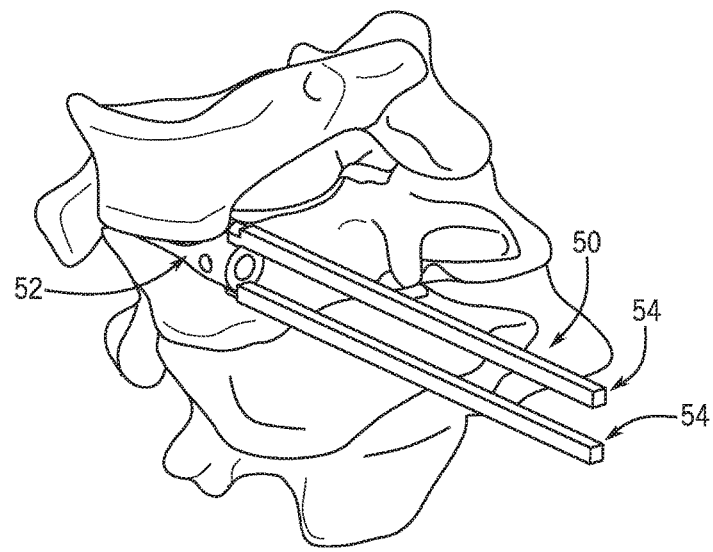
FIGS. 9A-9C are various views of a portion of a cervical spine, illustrating a system and method for inserting a lateral mass implant, according to an embodiment.
Figure 9B:
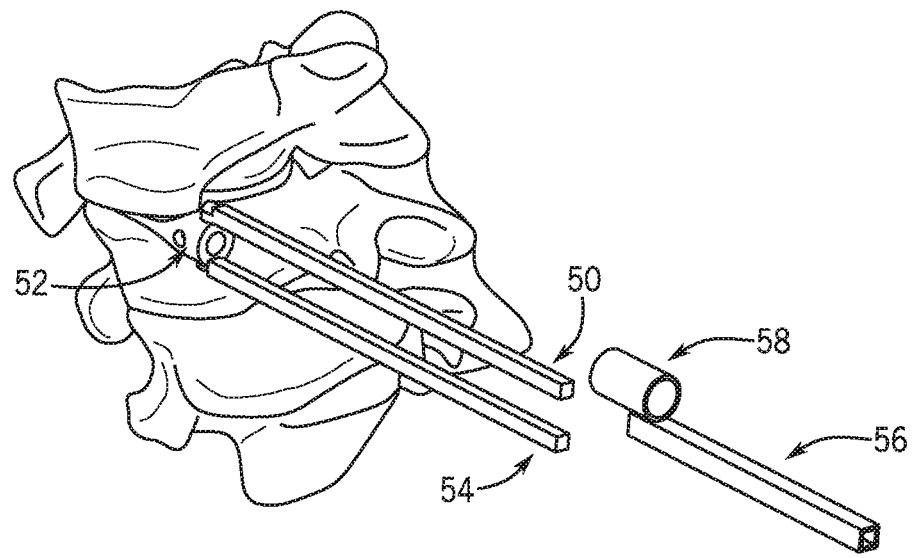
Figure 9C:
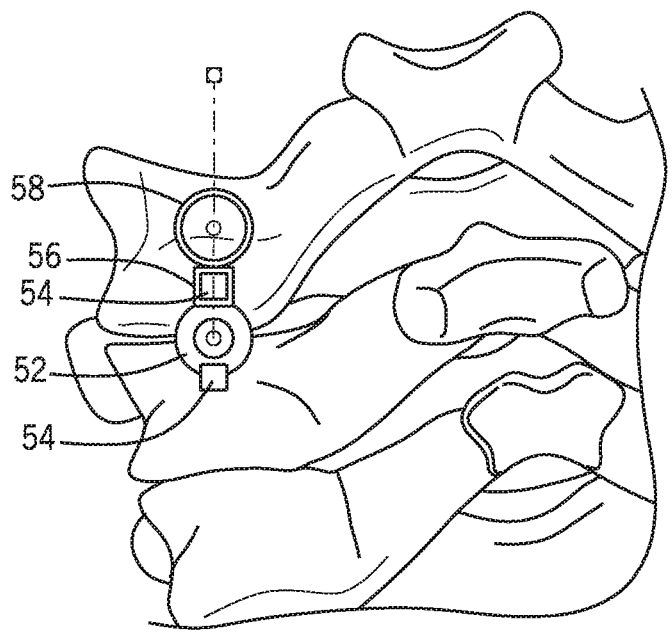

FIGS. 9A-9C illustrate yet another embodiment of a facet guide tool or device 50. Similar to the previously described embodiment, in this embodiment, the guide tool 50 includes a distal portion 52 and two or more proximal shafts 54. A guide system may further include a slidable guide instrument 56, with a side-mounted guide 58, which may be used to advance a screw (not shown) into bone. In this embodiment, the proximal shafts 54 have a square cross-sectional shape. As described above, the square cross-sectional shape may be used to orient the guide instrument 56 at 90-degree increments.

Figure 10A:
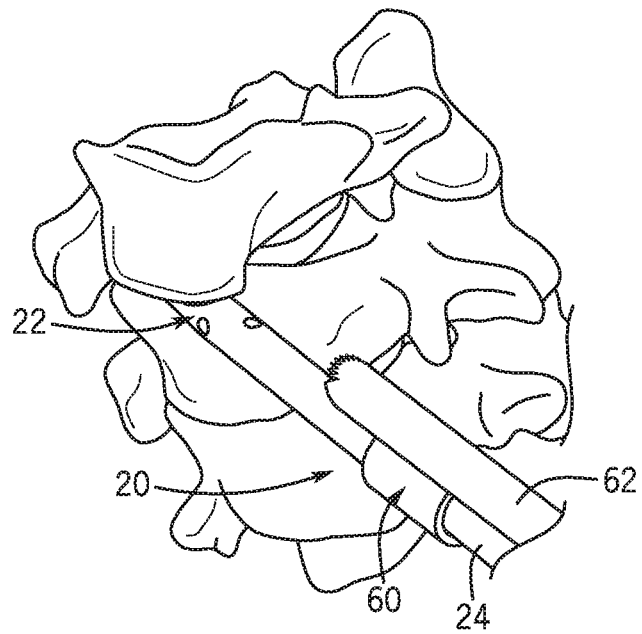
FIGS. 10A and 10B are perspective views of a portion of a cervical spine, illustrating a system and method for advancing a decorticator device over a guide device, according to one embodiment.
Figure 10B:
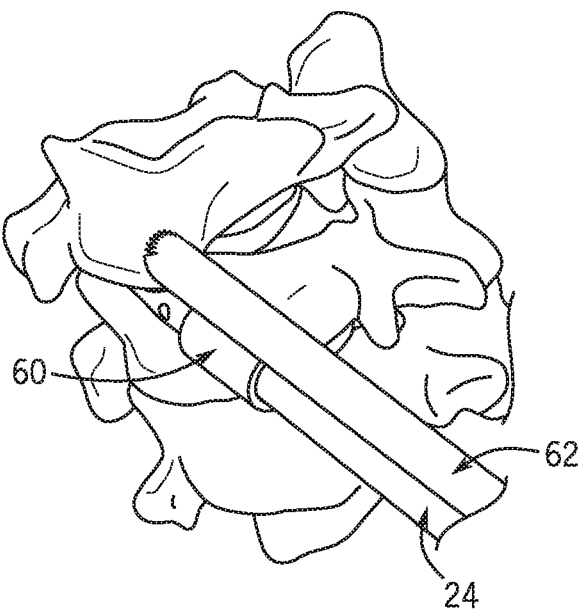

FIGS. 10A and 10B illustrate another instrument that may be advanced over a facet guide tool or device 20. In this embodiment, a slidable guide tube 60 with a side-mounted decortication device 62 is shown advancing over the guide tool 20. The decortication tool 62 may be used to cut or decorticate vertebral bone, as part of a fixation procedure. Various embodiments may include this and/or any other similar instrumentation, such as but not limited to screws, staples, posts in the lateral masses, and/or the like. Additional instrumentation, such as a rod or plate, may also be advanced over the facet guide tool 20. Plates generally act as tension bands to connect the rostral and caudal facet and serves to limit flexion and extension as well as lateral bending.

Figure 11A:
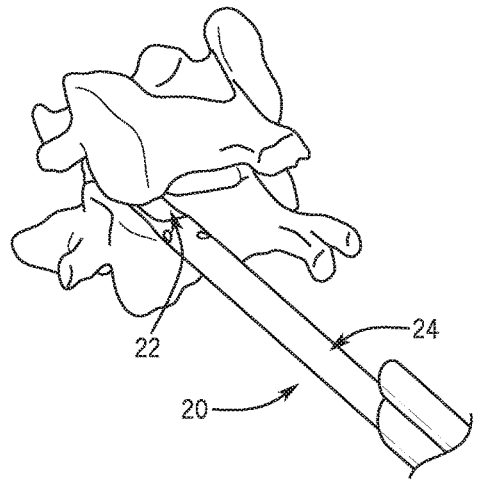
FIGS. 11A-11D are perspective views of a portion of a cervical spine, illustrating a system and method for advancing a drill through a guide device, according to one embodiment.
Figure 11B:
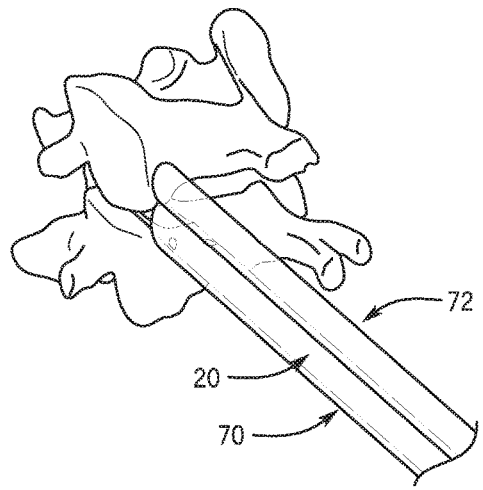
Figure 11C:
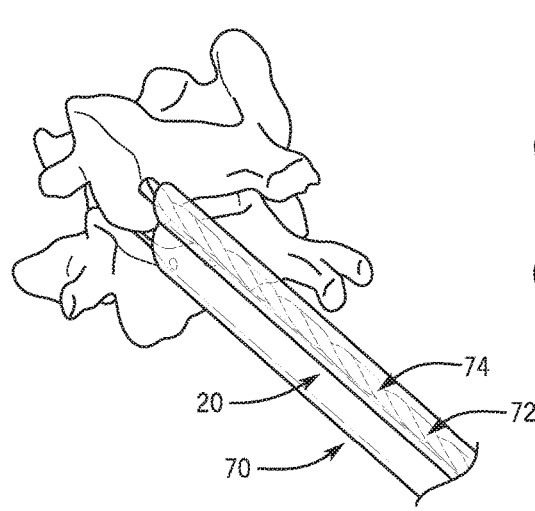
Figure 11D:
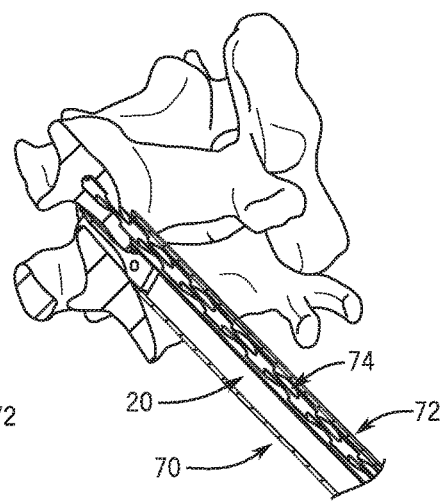

Referring now to FIGS. 11A-11D, in another embodiment, the facet guide tool or device 20 may be used to advance a double-barreled or dual-lumen guide tube device 70, having a side-mounted tube 72, to the cervical spine. As illustrated in FIGS. 11C and 11D, in one embodiment, a drill 74 may be advanced through the side-mounted tube. This guide tube device 70 thus allows for drilling of the lateral mass at the same angle as the facet.

Figure 12:
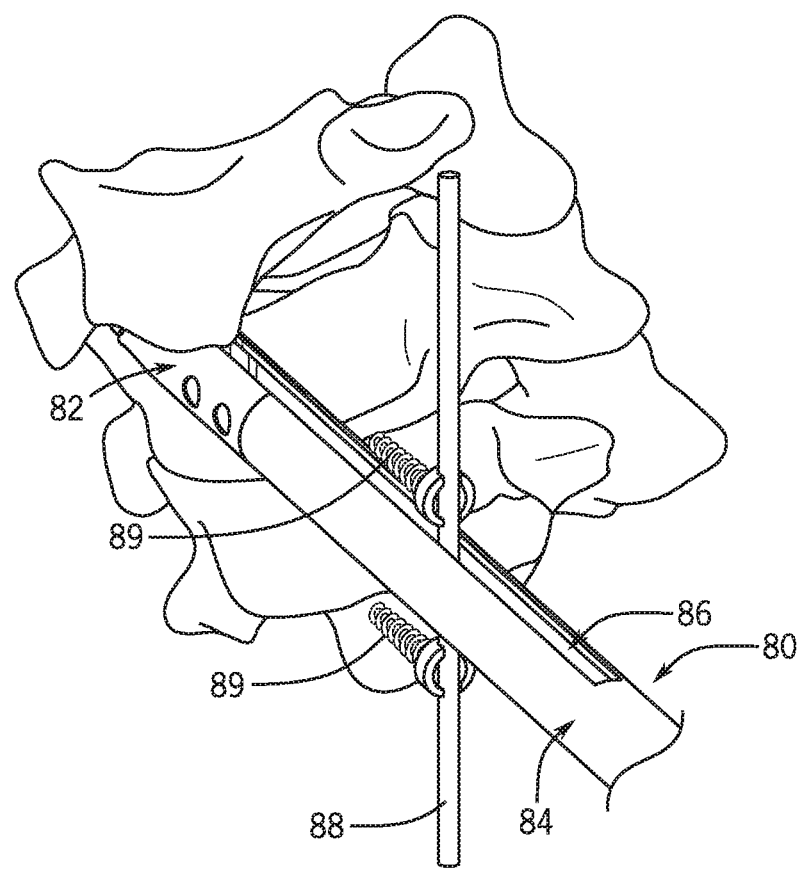
FIG. 12 is a perspective view of a portion of a cervical spine, illustrating a system and method for inserting a lateral mass implant, according to an embodiment.

In yet another embodiment, and with reference to FIG. 12, a facet guide tool 80 may have a distal portion 82 and a proximal shaft portion 84, including a slot 86. The slot 86 may be used for advancing a fixation device, such as rod 88 (or plate) and screws 89 for attachment to the rostral and caudal lateral mass.

Figure 13A:
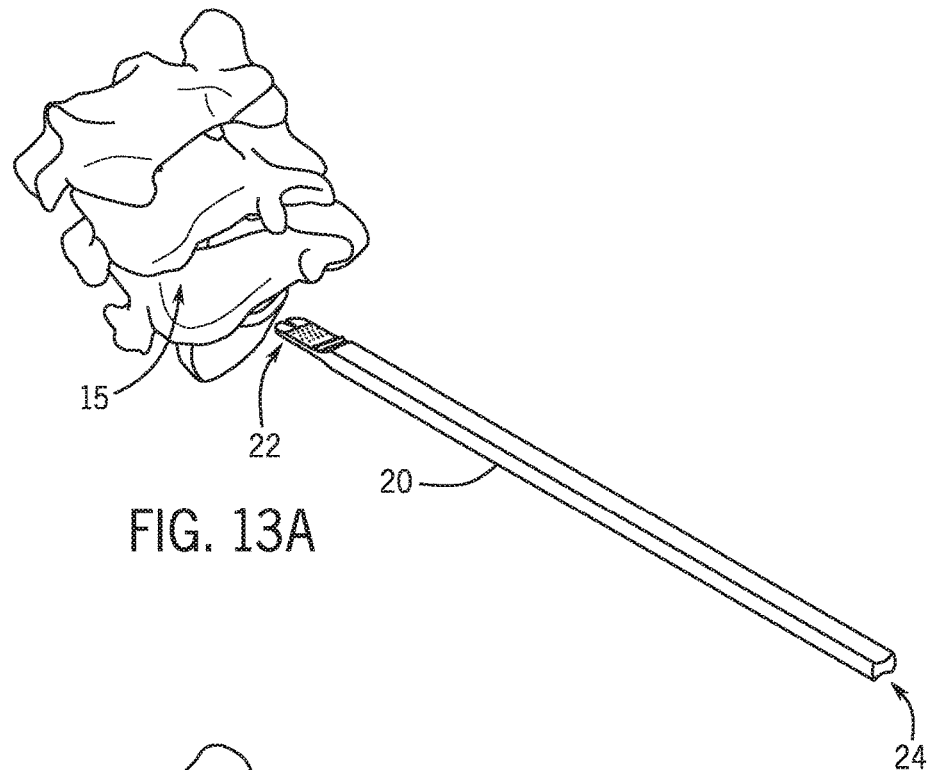
FIGS. 13A-13N illustrate various views of a portion of a cervical spine, illustrating a system and method for inserting a lateral mass implant, according to an embodiment.
Figure 13B:
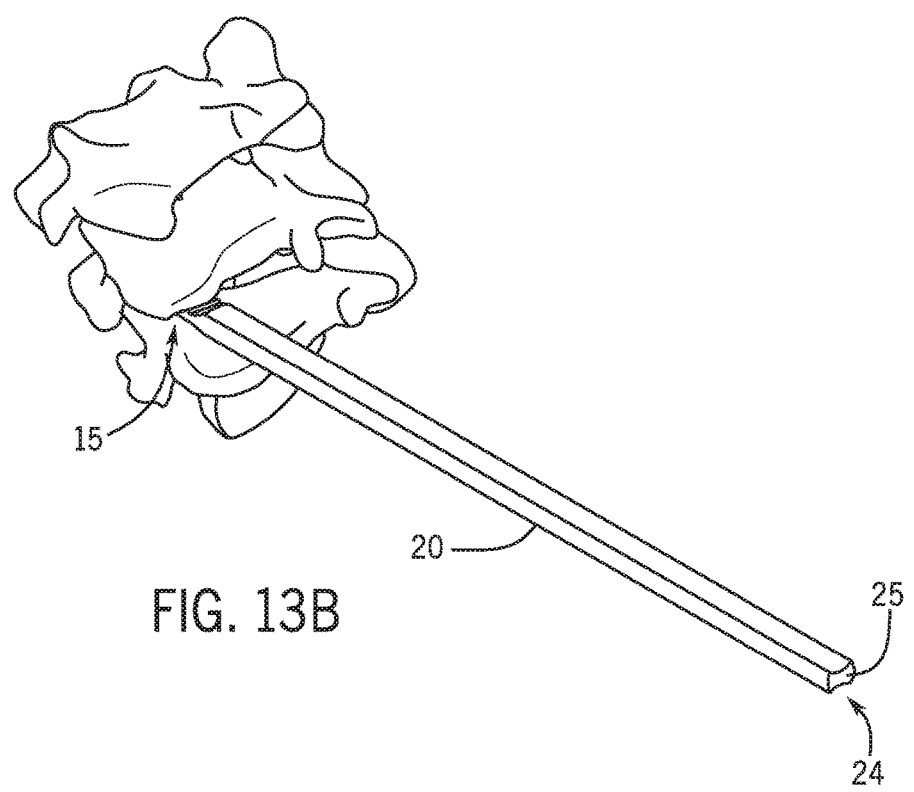
Figure 13C:
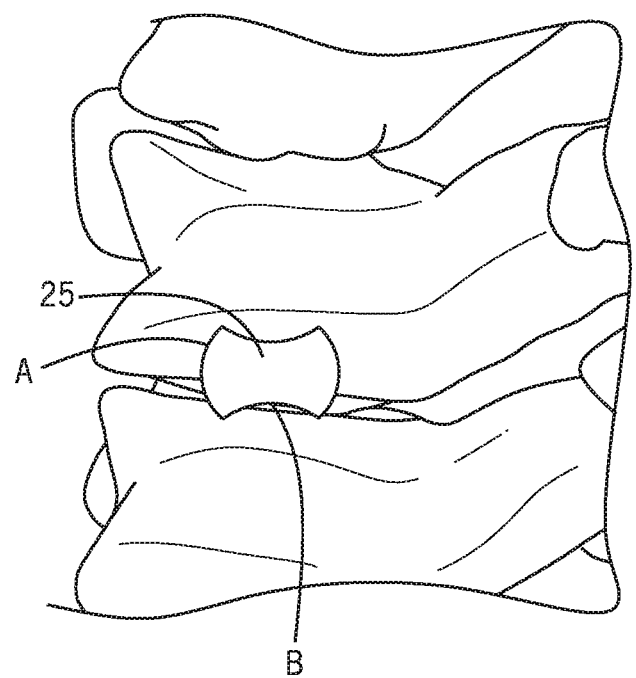
Figure 13D:
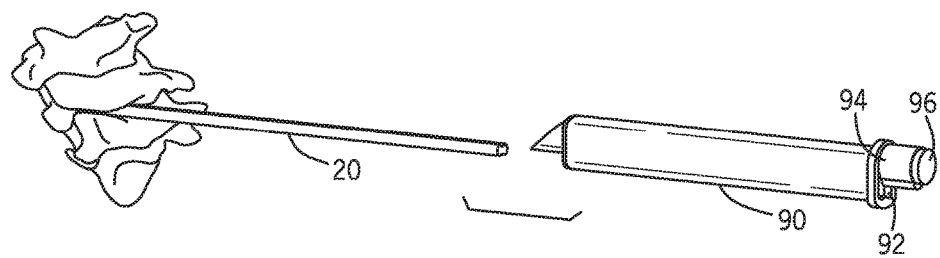
Figure 13E:
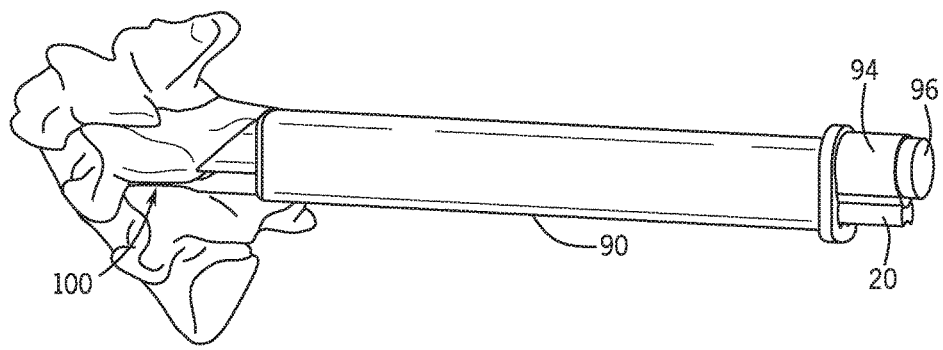
Figure 13F:
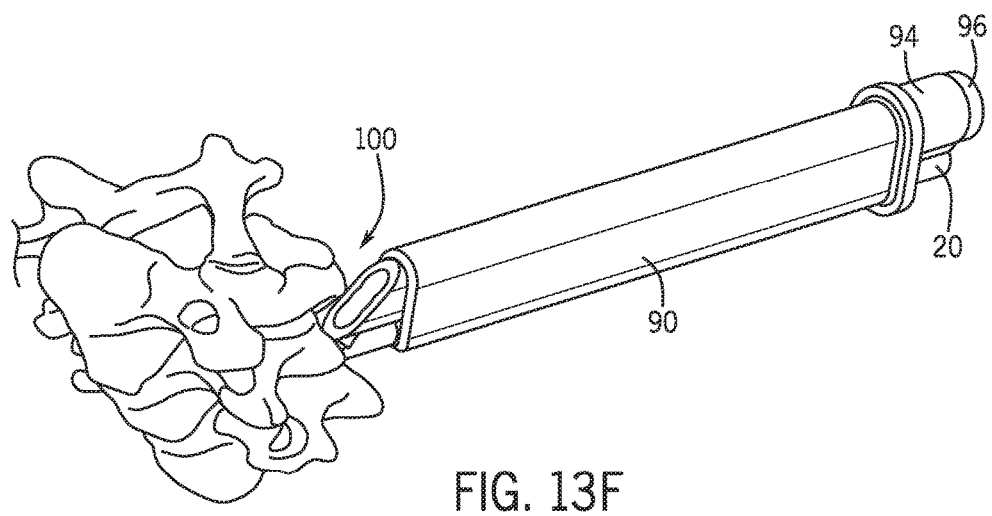
Figure 13G:
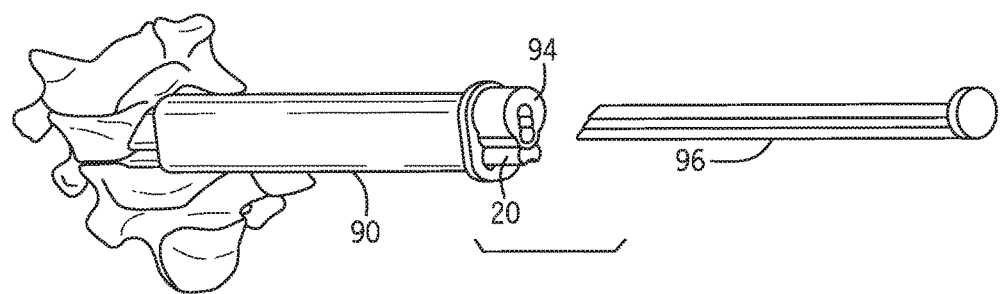
Figure 13H:
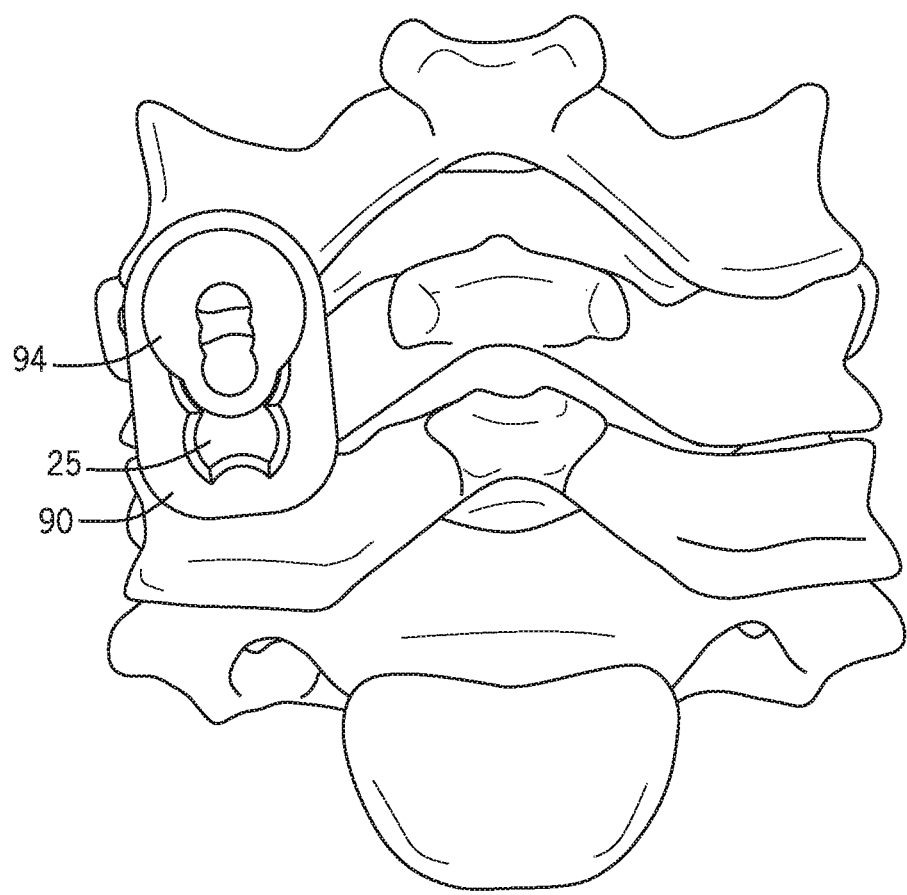
Figure 13I:
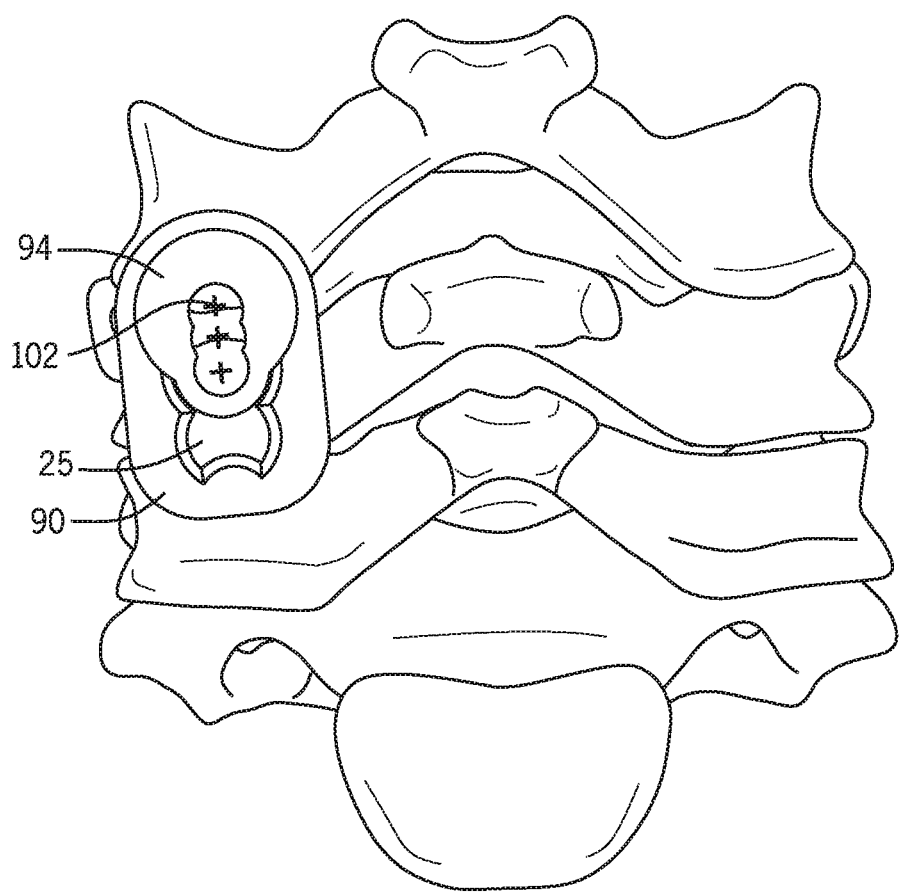
Figure 13J:
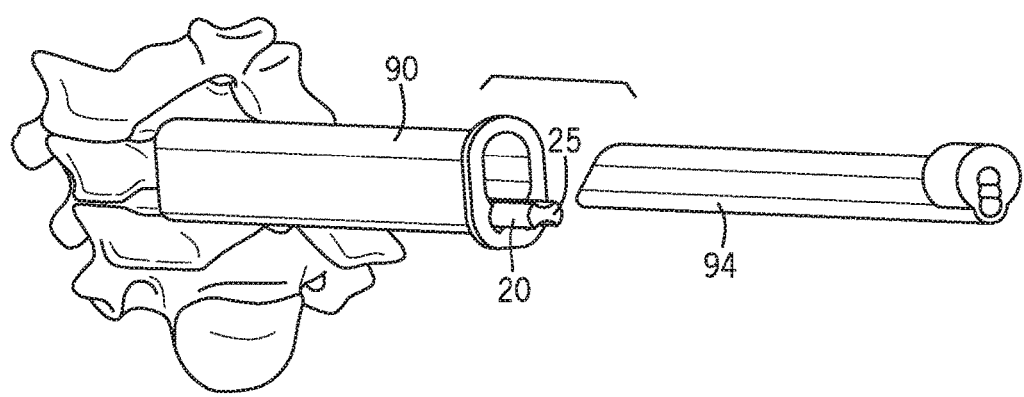
Figure 13K:
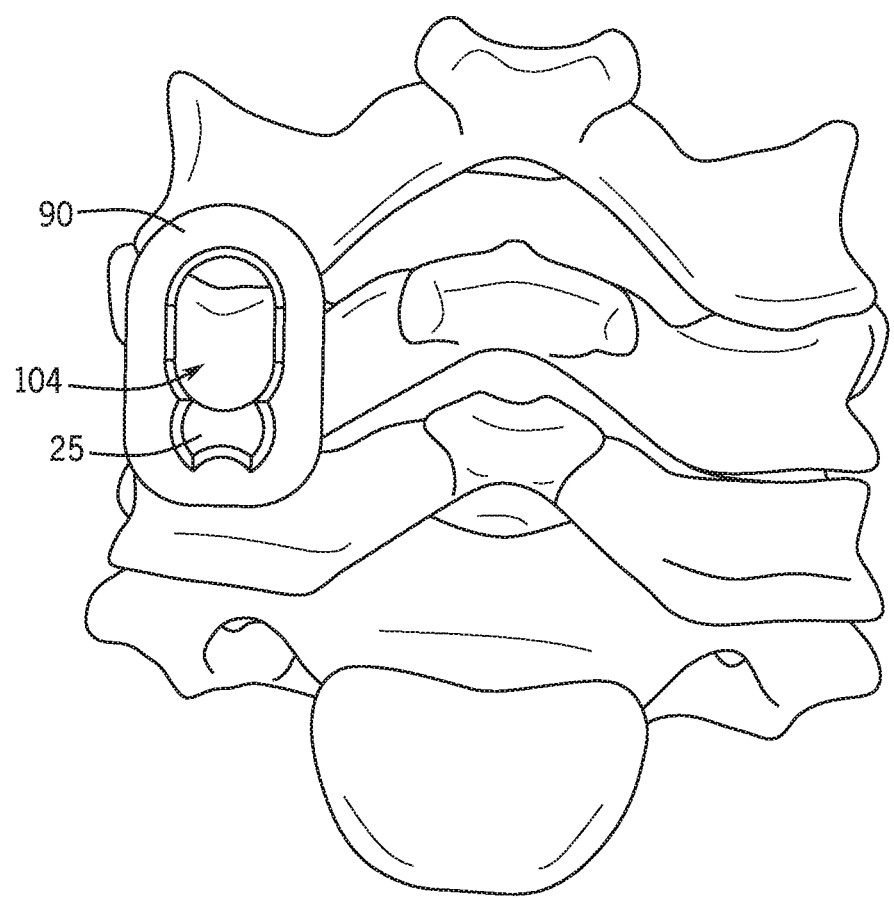
Figure 13L:
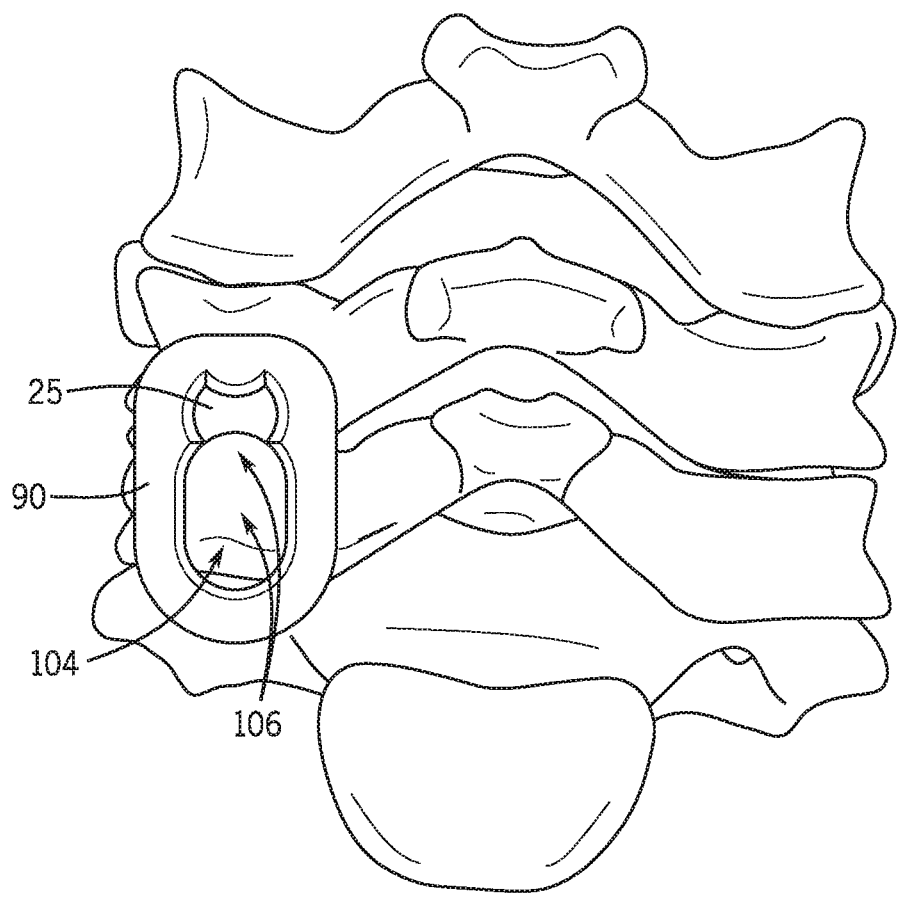
Figure 13M:
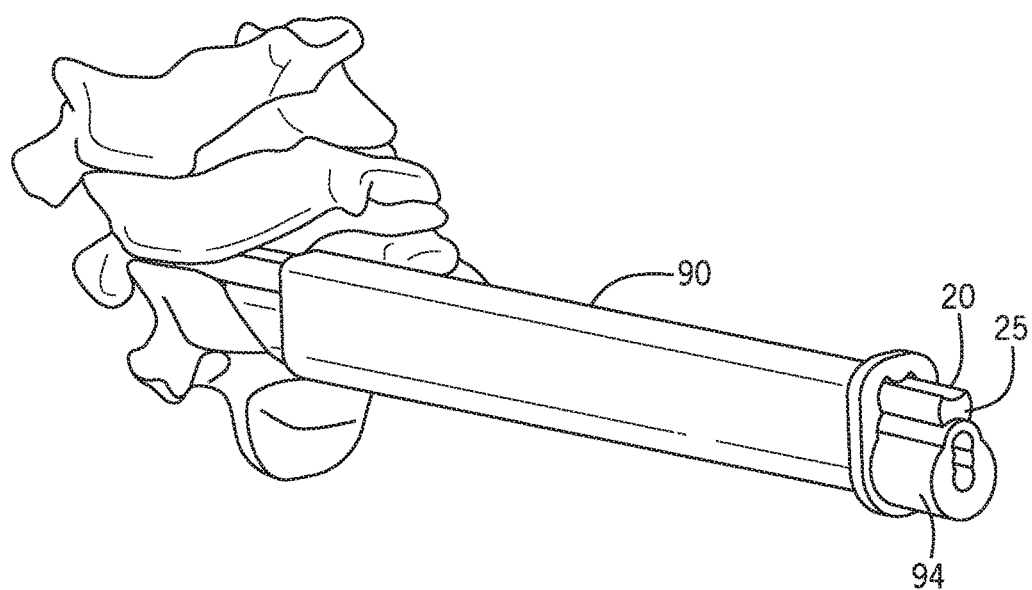
Figure 13N:
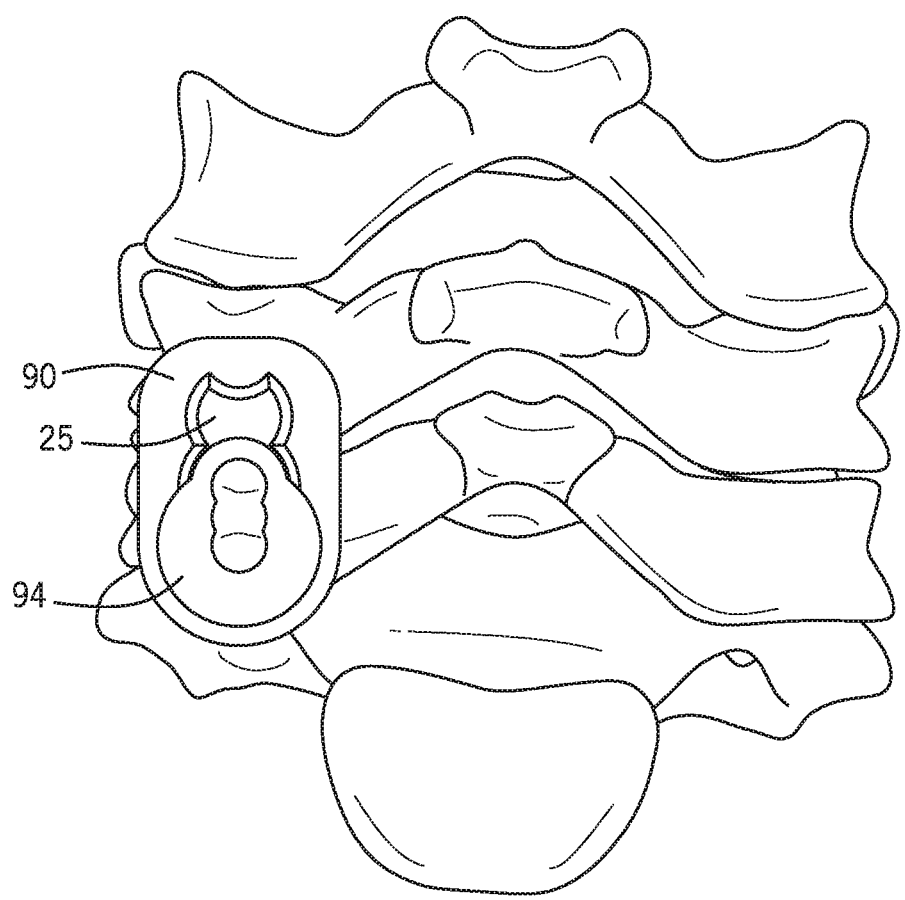

With reference to FIGS. 13A-13N, in one embodiment, a system for accessing and attaching fixation devices to a cervical spine facet 15 may include the guide tool 20 with distal portion 22 and proximal portion 24, as described above (see FIGS. 13A-13B). FIG. 13C illustrates a proximal end 25 of the tool 20 having opposing sides with a concave shape (A) and a convex shape (B). This shaped proximal end helps to maximize accessible lateral mass area and to lock the rotational position of a sliding guide tube 90 shown in later figures. As indicated in FIG. 13D and others, the system may also include an outer, sliding guide tube 90 defining a dual-lumen 92 for receiving both a drill guide 94 and stylet 96 and the guide tool 20.

In use, and as shown in FIGS. 13D-13F, the sliding guide tube 90 may be positioned over and slid onto the proximal portion 24 of the guide device 20, and docked or otherwise stabilized on or at the superior lateral mass 100. The stylet 96 may be removed from the drill guide 94 (FIG. 13G). FIG. 13H depicts an end view of the guide tool 20 and the drill guide 94 within the dual lumen 92 of the sliding guide tube 90. As discussed above, the shape of the tool 20 limits rotational movement of the guide tube 90. As illustrated in FIG. 13I, the drill guide 94 provides one or more guide paths 102 through which a drill, such as drill 74 in FIG. 11C, may be advanced through the guide 94. This guide tube device 90 thus allows for drilling of the lateral mass at or about the same angle as the facet. After drilling the pilot hole for a lateral mass screw, the drill guide 94 is removed from the guide tube 90 (FIG. 13J). As shown in FIG. 13K, a first lumen 104 of the dual lumen tube 90 now provides an opening through which a lateral mass screw (not shown) may be guided for insertion in the pre-drilled location. In some embodiments, a secondary guide tube could be used in the lumen 104 to more precisely guiding the screw to the pre-drilled location.

FIGS. 13L-13N illustrate the guide tool 20, sliding guide tube 90 and the drill guide 94 inserted in an opposite or rotated orientation (e.g. rotated 180° about the longitudinal axis of the guide tool 20) for use and screw insertion in the inferior lateral mass 106.

The C7 and T1 and T2 facets have a fixed relationship to the pedicle. All of the above devices, systems and methods may be used to cannulate the pedicle percutaneously, similar to that described for the lateral mass.

All relative and directional references (including: upper, lower, upward, downward, left, right, leftward, rightward, top, bottom, side, above, below, front, middle, back, vertical, horizontal, and so forth) are given by way of example to aid the reader's understanding of the particular embodiments described herein. They should not be read to be requirements or limitations, particularly as to the position, orientation, or use unless specifically set forth in the claims. Connection references (e.g., attached, coupled, connected, joined, and the like) are to be construed broadly and may include intermediate members between a connection of elements and relative movement between elements. As such, connection references do not necessarily infer that two elements are directly connected and in fixed relation to each other, unless specifically set forth in the claims.

Although the invention has been disclosed in the context of certain embodiments and examples, the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

What is claimed is:

1. A facet guide device for accessing and guiding at least one fixation device to a cervical spine via a posterior approach, the device comprising an elongated body comprising:
    a distal portion comprising a chamfered or beveled end portion configured for insertion in a facet joint of the cervical spine; and
    a proximal shaft portion extending from the distal portion, and having a first set of opposing sides extending at least a portion of a length of the elongated body, and a shaped proximal end,
    wherein the shaped proximal end maximizes accessible lateral mass area,
    wherein at least one side of the first set of opposing sides has a complementary shape to at least one lumen of a slidable guide device comprising at least two lumens coupled together and having parallel and distinct central longitudinal axes, the slidable guide device configured to receive and guide a fixation device to the cervical spine, and
    wherein the elongated body of the facet guide device decreases in height from the shaped proximal end to the distal portion along the length of the elongated body.

2. A device as in claim 1, wherein the distal and proximal portions are solid.

3. A device as in claim 1, wherein the shaped proximal end of the proximal shaft portion includes opposing sides having a concave shape.

4. A device as in claim 3, wherein the shaped proximal end of the proximal shaft portion includes opposing sides having a convex shape.

5. A device as in claim 1, wherein the first set of opposing sides extending at least a portion of a length of the body has a convex shape.

6. A device as in claim 1, wherein the proximal shaft portion further comprises a second set of opposing sides extending at least a portion of a length of the body, the second set of opposing sides having a concave shape.

7. A device as in claim 1, wherein the first set of opposing sides each define a recess extending at least a portion of the length of the elongated body.

8. A system for accessing and guiding at least one fixation device to adjacent vertebrae of a cervical spine via a posterior approach, the system comprising:
    a facet guide device, comprising an elongated body comprising:
        a distal portion comprising a chamfered or beveled end portion configured for insertion in a facet joint of the cervical spine; and
        a proximal shaft portion extending from the distal portion, and having:
            a first set of opposing sides extending at least a portion of a length of the elongated body, and
            a shaped proximal end, wherein the shaped proximal end maximizes accessible lateral mass area;
    a slidable guide device defining at least two lumens coupled together and having parallel and distinct central longitudinal axes, the slidable guide device slidingly received by the facet guide device and configured to receive and guide at least one instrument to the spine; and
    a fixation device,
    wherein at least one side of the first set of opposing sides of the facet guide device is complementary in shape to at least one lumen of the at least two lumens of the slidable guide device, and
    wherein the elongated body of the facet guide device decreases in height from the shaped proximal end to the distal portion along the length of the elongated body.

9. A system as in claim 8, wherein the at least two lumens of the slidable guide device comprise a double-barreled or dual-lumen guide tube.

10. A system as in claim 8, further comprising a drill guide having at least one drill path defined therein, the drill guide configured to be received by both the slidable guide device and the facet guide device.

11. A system as in claim 8, wherein the proximal shaft portion further comprises a second set of the opposing sides extending at least a portion of a length of the elongated body, the second set of opposing sides having a concave shape.

12. A system as in claim 8, wherein the first set of opposing sides extending at least a portion of a length of the elongated body has a convex shape.

13. A system as in claim 8, wherein the at least two lumens of the slidable guide device comprise:
    a first lumen for sliding over the proximal portion of the facet guide device; and
    a second lumen positioned proximate the first lumen for guiding and receiving the at least one instrument.

14. A system as in claim 8, wherein the fixation device comprises at least one bone screw, and the at least one bone screw is advanced through the slideable guide device.

15. A system as in claim 8, wherein the fixation device comprises a lateral mass screw or a pedicle screw.

16. A method for accessing and guiding at least one fixation device to adjacent vertebrae of a cervical spine via a posterior approach, the method comprising:
    advancing a guide device into a facet between two adjacent vertebrae, the guide device comprising an elongated body comprising a distal portion comprising a chamfered or beveled end portion configured for insertion in a facet joint of the cervical spine; and a proximal shaft portion extending from the distal portion, and having a first set of opposing sides extending at least a portion of a length of the elongated body, and a shaped proximal end, wherein the shaped proximal end maximizes accessible lateral mass area and at least one side of the first set of opposing sides is complementary in shape to at least one of at least two lumens of a slidable guide device, the at least two lumens coupled together and having parallel and distinct central longitudinal axes, the slidable guide device configured to receive and guide a fixation device to the cervical spine and wherein the elongated body of the facet guide device decreases in height from the shaped proximal end to the distal portion along the length of the elongated body;
    advancing a fixation device along the guide device; and
    attaching the fixation device to at least one of the two adjacent vertebrae.

17. A method as in claim 16, wherein attaching the fixation device comprises one of attaching a plate to a facet implant located in the facet or attaching a plate to the two adjacent vertebrae.

* * * * *